US010821000B2

(12) United States Patent
Gallagher et al.

(10) Patent No.: US 10,821,000 B2
(45) Date of Patent: Nov. 3, 2020

(54) TITANIUM IMPLANT SURFACES FREE FROM ALPHA CASE AND WITH ENHANCED OSTEOINDUCTION

(71) Applicant: Titan Spine, Inc., Mequon, WI (US)

(72) Inventors: Michelle B. Gallagher, Mequon, WI (US); Mark E. Berg, Mequon, WI (US); Jennifer M. Schneider, Mequon, WI (US)

(73) Assignee: Titan Spine, Inc., Mequon, WI (US)

( * ) Notice: Subject to any disclaimer, the term of this patent is extended or adjusted under 35 U.S.C. 154(b) by 0 days.

(21) Appl. No.: 16/318,961

(22) PCT Filed: Jun. 29, 2017

(86) PCT No.: PCT/US2017/039977
§ 371 (c)(1),
(2) Date: Jan. 18, 2019

(87) PCT Pub. No.: WO2018/026448
PCT Pub. Date: Feb. 8, 2018

(65) Prior Publication Data
US 2019/0231535 A1 Aug. 1, 2019

Related U.S. Application Data

(60) Provisional application No. 62/370,459, filed on Aug. 3, 2016.

(51) Int. Cl.
*A61F 2/30* (2006.01)
*A61L 27/06* (2006.01)
(Continued)

(52) U.S. Cl.
CPC .......... *A61F 2/30767* (2013.01); *A61B 17/58* (2013.01); *A61F 2/2846* (2013.01);
(Continued)

(58) Field of Classification Search
CPC ...... A61F 2/30767; A61F 2/0077; A61F 2/28; B23K 15/0086; B23K 26/345; B23K 26/0015; B23K 15/0093
See application file for complete search history.

(56) References Cited

U.S. PATENT DOCUMENTS 3,650,861 A 3/1972 Angell
3,891,456 A 6/1975 Hohman et al.
(Continued)

FOREIGN PATENT DOCUMENTS

CN 102300518 A 12/2011
EP 947605 10/1999
(Continued)

OTHER PUBLICATIONS

Astra Tech Dental "Nanolevel topogrpahic modifications on the OsseoSpeed surface", http://shop.dentsplyimplants.us, Mar. 8, 2001.
(Continued)

*Primary Examiner* — Jason-Dennis N Stewart
(74) *Attorney, Agent, or Firm* — Womble Bond Dickinson (US) LLP

(57) ABSTRACT

An orthopedic implant having a titanium or titanium alloy body with a plurality of surfaces. The orthopedic implant is produced according to a process comprising the steps of: (a) additively building the orthopedic implant; and then (b) mechanically, chemically, or mechanically and chemically eroding one or more surfaces of the orthopedic implant to (i) remove alpha case from, and (ii) impart an osteoinducting roughness including micro-scale structures and nano-scale structures into, the one or more surfaces.

20 Claims, 16 Drawing Sheets

(51) Int. Cl.
*A61L 27/50* (2006.01)
*A61B 17/58* (2006.01)
*A61F 2/28* (2006.01)

(52) U.S. Cl.
CPC ............... *A61L 27/06* (2013.01); *A61L 27/50* (2013.01); *A61F 2/3094* (2013.01); *A61F 2002/3084* (2013.01); *A61F 2002/3093* (2013.01); *A61F 2002/3097* (2013.01); *A61F 2002/30838* (2013.01); *A61F 2002/30968* (2013.01); *A61F 2002/30985* (2013.01); *A61L 2400/18* (2013.01)

(56) References Cited

U.S. PATENT DOCUMENTS

| | | | |
|---|---|---|---|
| 3,933,961 A | 1/1976 | Burns | |
| 4,116,755 A | 9/1978 | Coggins et al. | |
| 4,314,876 A | 2/1982 | Kremer et al. | |
| 4,414,039 A | 11/1983 | Thoma | |
| 4,540,465 A | 9/1985 | Coggins et al. | |
| 4,588,480 A | 5/1986 | Thoma | |
| 4,634,603 A | 1/1987 | Gruss et al. | |
| 4,644,942 A | 2/1987 | Sump | |
| 4,673,409 A | 6/1987 | Van Kampen | |
| 4,803,098 A | 2/1989 | Henri et al. | |
| 4,818,559 A | 4/1989 | Hama | |
| 4,818,572 A | 4/1989 | Shimamune et al. | |
| 4,834,756 A | 5/1989 | Kenna | |
| 4,846,837 A | 7/1989 | Kurze et al. | |
| 4,863,475 A | 9/1989 | Andersen et al. | |
| 4,900,398 A | 2/1990 | Chen | |
| 5,100,508 A | 3/1992 | Yoshida et al. | |
| 5,108,432 A * | 4/1992 | Gustavson | A61F 2/30734 623/23.54 |
| 5,201,766 A * | 4/1993 | Georgette | A61F 2/30767 128/898 |
| 5,246,530 A | 9/1993 | Bugle et al. | |
| 5,258,098 A | 11/1993 | Wagner et al. | |
| 5,411,629 A | 5/1995 | Warfield | |
| 5,456,723 A | 10/1995 | Steinemann et al. | |
| 5,571,188 A | 11/1996 | Ellingsen et al. | |
| 5,603,338 A | 2/1997 | Beaty | |
| 5,639,536 A | 6/1997 | Yamazaki et al. | |
| 5,705,082 A | 1/1998 | Hinson | |
| 5,787,965 A | 8/1998 | Sterett et al. | |
| 5,922,029 A | 7/1999 | Wagner et al. | |
| 6,033,582 A | 3/2000 | Lee et al. | |
| 6,068,043 A | 5/2000 | Clark | |
| 6,096,107 A | 8/2000 | Caracostas et al. | |
| 6,193,762 B1 | 2/2001 | Wagner et al. | |
| 6,491,723 B1 | 12/2002 | Beaty | |
| 6,620,332 B2 | 9/2003 | Amrich | |
| 6,652,765 B1 | 11/2003 | Beaty | |
| 6,810,939 B2 | 11/2004 | Roche et al. | |
| 6,911,249 B2 | 6/2005 | Wagner et al. | |
| 7,048,870 B1 | 5/2006 | Ellingsen et al. | |
| 7,067,169 B2 | 6/2006 | Liu et al. | |
| 7,079,914 B2 | 7/2006 | Berggren | |
| 7,087,085 B2 | 8/2006 | Steinemann et al. | |
| 7,144,428 B2 | 12/2006 | Anitua | |
| 7,166,129 B2 | 1/2007 | Michelson | |
| 7,241,313 B2 | 7/2007 | Unwin et al. | |
| 7,368,065 B2 | 5/2008 | Yang et al. | |
| 7,374,642 B2 | 5/2008 | Deutchman et al. | |
| 7,445,640 B2 | 11/2008 | Despres, III et al. | |
| 7,497,876 B2 | 3/2009 | Tuke et al. | |
| 7,501,073 B2 | 3/2009 | Wen et al. | |
| 7,537,664 B2 | 5/2009 | O'Neill et al. | |
| 7,615,078 B2 | 11/2009 | White et al. | |
| 7,648,727 B2 | 1/2010 | Hossainy et al. | |
| 7,662,190 B2 | 2/2010 | Steinemann et al. | |
| 7,771,774 B2 | 8/2010 | Berckmans, III et al. | |
| 7,824,462 B2 | 11/2010 | Webster et al. | |
| 7,901,462 B2 | 3/2011 | Yang et al. | |
| 7,951,285 B2 | 5/2011 | Zipprish | |
| 7,972,648 B2 | 7/2011 | Berckmans, III et al. | |
| 8,052,743 B2 | 11/2011 | Weber et al. | |
| 8,277,577 B2 | 10/2012 | Garcia Saban et al. | |
| 8,309,162 B2 | 11/2012 | Charlton et al. | |
| 8,334,044 B2 | 12/2012 | Myung et al. | |
| 8,350,186 B2 | 1/2013 | Jones et al. | |
| 8,409,655 B2 | 4/2013 | Uibel et al. | |
| 8,444,914 B2 | 5/2013 | Fecher et al. | |
| 8,486,319 B2 | 7/2013 | Victor et al. | |
| 8,590,157 B2 | 11/2013 | Kruth et al. | |
| 8,632,836 B2 | 1/2014 | Fredriksson et al. | |
| 8,632,843 B2 | 2/2014 | Andersson et al. | |
| 8,641,418 B2 | 2/2014 | Mayfield et al. | |
| 8,679,517 B2 | 3/2014 | Palmaz | |
| 8,696,759 B2 | 4/2014 | Tong et al. | |
| 8,778,443 B2 | 7/2014 | Uckelmann et al. | |
| 8,808,385 B1 | 8/2014 | Smith et al. | |
| 8,814,939 B2 | 8/2014 | Ullrich, Jr. et al. | |
| 8,843,229 B2 | 9/2014 | Vanasse et al. | |
| 9,028,584 B2 | 5/2015 | Wong | |
| 9,044,528 B2 | 6/2015 | Esat et al. | |
| 9,135,374 B2 | 9/2015 | Jones et al. | |
| 9,149,989 B2 | 10/2015 | Uckelmann | |
| 9,174,390 B2 | 11/2015 | Lechmann et al. | |
| 9,192,475 B2 | 11/2015 | Chaput et al. | |
| 9,237,950 B2 | 1/2016 | Hensley et al. | |
| 9,249,055 B2 | 2/2016 | Laughner et al. | |
| 9,775,711 B2 | 10/2017 | Li et al. | |
| 9,848,995 B2 | 12/2017 | Ullrich, Jr. et al. | |
| 2002/0156529 A1 | 10/2002 | Li et al. | |
| 2002/0173854 A1 | 11/2002 | Amrich | |
| 2003/0125739 A1 | 7/2003 | Bagga et al. | |
| 2004/0134886 A1 | 7/2004 | Wagner et al. | |
| 2004/0153154 A1 | 8/2004 | Dinkelacker | |
| 2004/0167632 A1 | 8/2004 | Wen et al. | |
| 2004/0265780 A1 | 12/2004 | Robb et al. | |
| 2005/0062033 A1 | 3/2005 | Ichihara et al. | |
| 2005/0147942 A1 | 7/2005 | Hall | |
| 2005/0161120 A1 | 7/2005 | Inagaki et al. | |
| 2005/0221258 A1 | 10/2005 | Hall | |
| 2006/0004466 A1 | 1/2006 | Glocker et al. | |
| 2006/0100716 A1 | 5/2006 | Lerf | |
| 2006/0190079 A1 | 8/2006 | Istephanous et al. | |
| 2006/0219661 A1 | 10/2006 | Towse et al. | |
| 2006/0229715 A1 | 10/2006 | Istephanous | |
| 2006/0235534 A1 | 10/2006 | Gertzman et al. | |
| 2007/0166349 A1 | 7/2007 | White | |
| 2007/0203584 A1 | 8/2007 | Bandyopadhyay et al. | |
| 2007/0213832 A1 | 9/2007 | Wen | |
| 2007/0233248 A1 | 10/2007 | Schwab et al. | |
| 2007/0259427 A1 | 11/2007 | Storey et al. | |
| 2008/0014243 A1 | 1/2008 | Ellingsen et al. | |
| 2008/0154378 A1 | 6/2008 | Pelo | |
| 2008/0160259 A1 | 7/2008 | Nielson et al. | |
| 2008/0195218 A1 | 8/2008 | Jones | |
| 2009/0076613 A1 | 3/2009 | Biedermann et al. | |
| 2009/0088853 A1 | 4/2009 | Ogilvie et al. | |
| 2009/0132048 A1 | 5/2009 | Denzer | |
| 2009/0283701 A1 | 11/2009 | Ogawa | |
| 2009/0312842 A1 | 12/2009 | Bursac et al. | |
| 2010/0021865 A1 | 1/2010 | Uckelmann et al. | |
| 2010/0094426 A1 | 4/2010 | Grohowski, Jr. et al. | |
| 2010/0114303 A1 | 5/2010 | Su et al. | |
| 2010/0137990 A1 | 6/2010 | Apatsidis et al. | |
| 2010/0167020 A1 | 7/2010 | Jones et al. | |
| 2010/0168798 A1 | 7/2010 | Clineff et al. | |
| 2010/0173264 A1 | 7/2010 | Fredriksson et al. | |
| 2010/0174382 A1 | 7/2010 | Gretzer et al. | |
| 2010/0204777 A1 | 8/2010 | Storey et al. | |
| 2010/0218854 A1 | 9/2010 | Garcia Saban et al. | |
| 2010/0268227 A1 | 10/2010 | Tong et al. | |
| 2010/0303722 A1 | 12/2010 | Jin et al. | |
| 2011/0009965 A1 | 1/2011 | Ankem | |
| 2011/0014081 A1 | 1/2011 | Jones et al. | |
| 2011/0033661 A1 | 2/2011 | Oawa | |
| 2011/0035020 A1 | 2/2011 | Laughner et al. | |
| 2011/0089041 A1 | 4/2011 | Gupta et al. | |
| 2011/0151026 A1 | 6/2011 | Hansson et al. | |

(56) References Cited

U.S. PATENT DOCUMENTS

| | | |
|---|---|---|
| 2011/0190888 A1 | 8/2011 | Bertele et al. |
| 2011/0190902 A1 | 8/2011 | Tong et al. |
| 2011/0190904 A1 | 8/2011 | Lechmann et al. |
| 2011/0233169 A1 | 9/2011 | Mayfield et al. |
| 2011/0282454 A1 | 11/2011 | Ullrich, Jr. et al. |
| 2011/0287223 A1 | 11/2011 | Victor et al. |
| 2011/0318835 A1 | 12/2011 | Chen et al. |
| 2012/0009341 A1 | 1/2012 | Noh et al. |
| 2012/0022650 A1 | 1/2012 | Gilbert et al. |
| 2012/0064290 A1 | 3/2012 | Esat et al. |
| 2012/0136396 A1 | 5/2012 | Baker et al. |
| 2012/0276336 A1 | 11/2012 | Malshe et al. |
| 2012/0303127 A1 | 11/2012 | Ullrich, Jr. et al. |
| 2012/0308837 A1 | 12/2012 | Schlechtriemen et al. |
| 2012/0310365 A1 | 12/2012 | Chaput et al. |
| 2012/0312778 A1 | 12/2012 | Ullrich, Jr. et al. |
| 2012/0312779 A1 | 12/2012 | Patterson et al. |
| 2012/0316650 A1 | 12/2012 | Ullrich, Jr. et al. |
| 2012/0316651 A1 | 12/2012 | Ullrich, Jr. et al. |
| 2013/0006363 A1 | 1/2013 | Ullrich, Jr. et al. |
| 2013/0030544 A1 | 1/2013 | Studer |
| 2013/0045360 A1 | 2/2013 | Ibacache et al. |
| 2013/0059946 A1 | 3/2013 | Zhu et al. |
| 2013/0110243 A1 | 5/2013 | Patterson et al. |
| 2013/0204384 A1 | 8/2013 | Hensley et al. |
| 2013/0244003 A1 | 9/2013 | Yoo et al. |
| 2013/0248487 A1 | 9/2013 | Mayfield et al. |
| 2013/0261764 A1 | 10/2013 | Guerra et al. |
| 2013/0264749 A1 | 10/2013 | Jones et al. |
| 2013/0292357 A1 | 11/2013 | Ullrich, Jr. et al. |
| 2013/0302427 A1 | 11/2013 | Arvidsson et al. |
| 2013/0306591 A1 | 11/2013 | Ullrich, Jr. et al. |
| 2013/0330688 A1 | 12/2013 | Hedrick et al. |
| 2014/0025181 A1 | 1/2014 | Vanasse et al. |
| 2014/0106144 A1 | 4/2014 | Wong |
| 2014/0172111 A1 | 6/2014 | Lang et al. |
| 2014/0195001 A1 | 7/2014 | Grohowski, Jr. |
| 2014/0277517 A1 | 9/2014 | Winslow |
| 2014/0343687 A1 | 11/2014 | Jennissen |
| 2015/0012109 A1 | 1/2015 | Moreau et al. |
| 2015/0030493 A1 | 1/2015 | Scott et al. |
| 2015/0045903 A1 | 2/2015 | Neal |
| 2015/0093719 A1 | 4/2015 | Beeby |
| 2015/0209094 A1 | 7/2015 | Anderson |
| 2015/0320525 A1 | 11/2015 | Lin et al. |
| 2015/0335434 A1 | 11/2015 | Patterson et al. |
| 2017/0071744 A1 | 3/2017 | Bali et al. |
| 2017/0165790 A1 | 6/2017 | McCarthy et al. |
| 2017/0281827 A1 | 10/2017 | Baker |
| 2017/0290666 A1 | 10/2017 | Behzadi |
| 2017/0290667 A1 | 10/2017 | Behzadi |
| 2018/0333782 A1 | 11/2018 | Gallagher et al. |
| 2019/0142574 A1 | 5/2019 | Quirós et al. |
| 2019/0231535 A1 | 8/2019 | Gallagher et al. |

FOREIGN PATENT DOCUMENTS

| | | |
|---|---|---|
| EP | 1440669 | 7/2004 |
| EP | 1449544 | 8/2004 |
| EP | 1947217 B1 | 7/2008 |
| EP | 2386274 A1 | 11/2011 |
| GB | 2523814 | 3/2014 |
| WO | 2004008983 | 1/2004 |
| WO | 2006102347 | 9/2006 |
| WO | 2007045471 | 4/2007 |
| WO | 2011/094604 | 8/2011 |
| WO | 2013126407 | 8/2013 |
| WO | 2013167904 | 11/2013 |
| WO | 2014/018325 | 1/2014 |
| WO | 2014028505 | 2/2014 |
| WO | 2014154901 | 10/2014 |
| WO | 2015132325 | 9/2015 |
| WO | 2015157703 | 10/2015 |
| WO | 2015164982 | 11/2015 |
| WO | 2017053480 | 3/2017 |
| WO | 2017062397 | 4/2017 |
| WO | 2017087927 | 5/2017 |
| WO | 2017091657 | 6/2017 |
| WO | 2017177046 | 10/2017 |

OTHER PUBLICATIONS

Boyan et al., "Implant Surface Design Regulates Mesenchymal Stem Cell Differentiation and Maturation", Advances in Dental Research, 2016, 28(1), pp. 10-17.

Cheng et al., "Additively Manufactured 3D Porous Ti—6Al—4V Constructs Mimic Trabecular Bone Structure and Regulate Osteoblast Proliferation, Differentiation and Local Factor Production in a Porosity and Surface Roughness Dependent Manner", Biofabrication, 6(4), 045007.

Cheng et al., "Laser-Sintered Constructs with Bio-inspired Porosity and Surface Micro/Nano-Roughness Enhance Mesenchymal Stem Cell Differentiation and Matrix Mineralization In Vitro", Calcif Tissue Int, 2016, 99(6), pp. 625-637.

Cohen et al., "Novel Osteogenic Ti—6Al—4V Device for Restoration of Dental Function in Patients With Large Bone Deficiencies: Design, Development, and Implementation", Scientific Reports, 2016, 6(20493), pp. 1-12.

E-Manufacturing Solutions, "Additive Manufactoring in the Medical Field", Medical, Mar. 2013, e-Manufactoring Solutions, Krailing/Munich Germany, www.eos.info.

Eurocoating, "Additive Manufacturing: long-term specialist expertise in manufactoring implantable devices", Additive Manufactoring, 2008, Eurocoating spa, Trento Italy, www.eurocoating.it.

Guo, et al., "The effect of hydrofluoric acid treatment of TiO2 grit blasted titanium implants on adherent osteoblast gene expression in vitro and in vivo", Biomaterials 28, Sep. 14, 2007, 5418-5425.

He, et al., "Mechanical and Histomorphometirc Evaluations of Rough Titanium Implants Treated with Hydrofluoric Acid/ Nitric Acid Solution in Rabbit Tibia", Int J. Oral Maxillofac., Implants, Nov. 1, 2011; 26; 115-122.

Hyzy et al., "Novel Hydrophilic Nanostructured Microtexture on Direct Metal Laser Sintered Ti—6Al—4V Surfaces Enhances Osteoblast Response in Vitro and Osseointegration in a Rabbit Model", J Biomed Mater Res A, 2016, 104 (8), pp. 2086-2098.

International Search Report by the European Patent Office for International Application No. PCT/US2017/039977 dated Sep. 26, 2017.

International Search Report by the European Patent Office for International Application No. PCT/US2017/039989 dated Sep. 6, 2017.

ipmd.net, "Powder Metallurgy Review", 2012, ipmd.net, pp. 1-32, www.ipmd.net.

Isa, et al., "Effects of Fluoride-Modified Titanium Surfaces on Osteoblast Proliferation and Gene Expression", Int. J. Oral Maxillofac, Implants, 2006, 21:203-211.

Lamolle et al., "The effect of hydrofluoric acid treatment of titanium surface on nanostructrual and chemical changes and the growth of MC3T3-E1 cells", Biomaterials 30 (Nov. 20, 2008) 736-742.

Layerwise, "Medical Applications", Layerwise, 2012, Belgium, www.layerwise.com, www.dentwise.eu.

Meirelles et al., "The Effect of Chemical and Nanotopographical Modifications on the Early Stages of Osseointegration", Int. J. Oral Maxillofac, Implants 2008, 23, 641-647.

Tammas-Williams et al., "The Effectiveness of Hot Isostatic Pressing for Closing Porosity in Titanium Parts Manufactured by Selective Electron Beam Melting," Metallurgical and Materials Transactions, vol. 47A, May 2016.

Variola et al., "Nanoscale surface modifications of medically relevant metals: state-of-the-art and prespectives", Nanoscale, 2011, 3, 335-353.

Wennerberg, A., et al., "Effects of titanium surface topogrpahy on bone intergration: a systematic review", Clin. Oral. Impl. Res. 20, (Suppl. 4), 2009, pp. 172-184.

Wennerberg, et al., "Spontaneoulsy formed nanostructures on titanium surfaces", Clin Oral Impl Res, 2012, 1-7.

(56) References Cited

OTHER PUBLICATIONS

"The Effects of Hot Isostatic Pressing of Platinum Alloy Castings on Mechanical Properties and Microstructures" Frye T, Johnson Matthey Technology Review, 2015, vol. 59, No. 3, pp. 207-217.
Baek, W-Y, et al. "Positive Regulation of Adult Bone Formation by Osteoblast-Specific Transcription Factor Osterix", Journal of Bone Mineral Research, Dec. 29, 2008, vol. 24, No. 6, pp. 1055-1065.
Zhang, C., "Transcriptional regulation of bone formation by the osteoblast-specific transcription factor Osx", Journal of Orthopaedic Surgery and Research, Jun. 15, 2010, vol. 5, No. 37.
Tu et al., "Osterix Overexpression in Mesenchymal Stem cells Stimulates Healing of Critical-Sized Defects in Murine Calvarial Bone", Tissue Engineering, Oct. 2007, vol. 13, No. 10, pp. 2431-2440.
Leung, K. S. et al. "Plasma Bone-Specific Alkaline Phosphatase as an Indicator of Osteoblastic Activity", Journal of Bone & Joint Surgery, Jul. 14, 1992, vol. 75, No. 2, pp. 288-292.
Herrmann et al., "Different Kinetics of Bone Markers in Normal and Delayed Fracture Healing of Long Bones", Clinical Chemistry, Dec. 2002, vol. 48, Issue 12, pp. 2263-2266.
Borden M, et al., "The sintered microsphere matrix for bone tissue engineering: In vitro osteoconductivity studies", Journal of Biomedical Materials Research, Dec. 2001, vol. 61, No. 3, pp. 421-429.
Borden M, et al., "Tissue engineered microsphere-based matrices for bone repair: design and evaluation", Biomaterials, Apr. 3, 2001, vol. 23, pp. 551-559.
Borden M, et al., "Tissue-engineered bone formation in vivo using a novel sintered polymeric microsphere matrix", Journal of Bone and Joint Surgery, Jan. 15, 2004, vol. 86, pp. 1200-1208.
Datta et al., "Effect of bone extracellular matrix synthesized in vitro on the osteoblastic differentiation of marrow stromal cells", Biomaterials, Jul. 21, 2004, vol. 26, No. 9, pp. 971-977.
Bancroft et al., "Fluid flow increases mineralized matrix deposition in 3D perfusion culture of marrow stromal osteoblasts in a dose-dependent manner", Proceedings of the National Academy of the Sciences of the U.S.A., Oct. 1, 2002, vol. 99, No. 20, pp. 12600-12605.
Sikavitsas et al., "Influence of the in vitro culture period on the in vivo performance of cell/titanium bone tissue-engineered constructs using a rat cranial critical size defect model", Journal of Biomedical Materials Research, Mar. 31, 2003, vol. 67, No. 3, pp. 944-951.
Hot Isostatic Pressing (HIP), Isostatic Pressing Association, http://ipa-web.org/about-ip/hip.html, Oct. 16, 2016 (IPA).
Koch, Carl C. (2007). Nanostructured Materials—Processing, Properties, and Applications (2nd Edition)—5.3.4.1 Hot Pressing. (pp. 210-211). William Andrew Publishing.
Matteson et al., "Assessing the hierarchical structure of titanium implant surfaces", May 7, 2015, Journal of Biomedical Materials Research B: Applied Biomaterials, vol. 00b, Issue 00.
Yavari et al., "Bone regeneration performance of surface-treated porous titanium", Biomaterials vol. 35, Issue 24, Aug. 2014, pp: 6172-6181.
Communication pursuant to Article 94(3) EPC dated Mar. 25, 2020, from European Appln. No. 17740181.7.
Anonymous: "Hot isostatic pressing—Wikipedia", Mar. 19, 2019 (Mar. 19, 2019), XP55571109; Retrieved from the internet: URL:https://en.wikipedia.org/wiki/Hot_isostatic-pressing [retrieved on Mar. 19, 2019].
Communication pursuant to Article 94(3) EPC dated Mar. 12, 2020, from European Appln. No. 16810533.6.
First office action dated Sep. 2, 2020 issued by the National Intellectual Property Administration of China for Patent Application No. 201780055177.3.

* cited by examiner 100.00 μm

FIG. 7A      0.1 mm

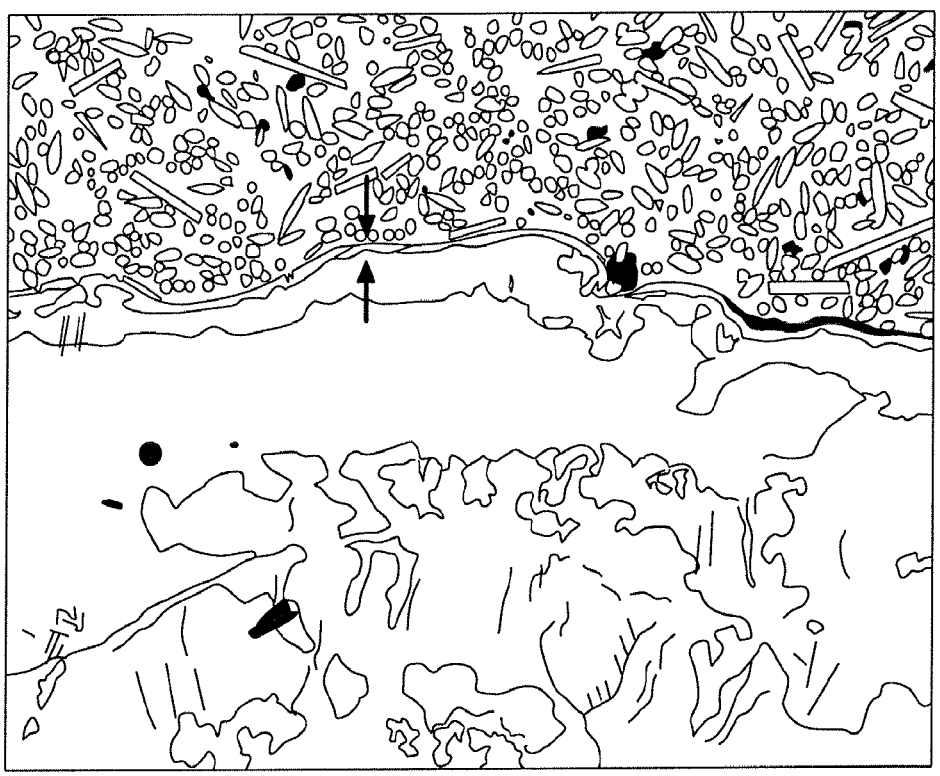
FIG. 7B  0.1 mm

FIG. 7C  0.1 mm

TITANIUM IMPLANT SURFACES FREE FROM ALPHA CASE AND WITH ENHANCED OSTEOINDUCTION

CROSS REFERENCE TO RELATED APPLICATION

This application claims the benefit of priority to U.S. Provisional Patent Application No. 62/370,459 filed on Aug. 3, 2016, the contents of which are incorporated in this document by reference.

FIELD OF THE INVENTION

The invention relates generally to the field of orthopedic implants. In particular, the invention relates to metal surfaces for orthopedic implants, which upon implantation within the body stimulate mesenchymal stem cells to differentiate into preosteoblasts, and stimulate preosteoblasts to mature into osteoblasts, thereby facilitating new bone growth. The surfaces are prepared by a combination of an additive manufacture process followed by secondary processing. The surfaces are free from alpha case.

BACKGROUND OF THE INVENTION

Various publications, including patents, published applications, technical articles, and scholarly articles are cited throughout the specification. Each of these cited publications is incorporated by reference herein, in its entirety and for all purposes.

Various orthopedic implants are used to correct skeletal defects. In many cases, integration of the implant with adjacent bone is desired, though not easily achieved. For example, it is known that certain polymeric materials such as polyether ether ketone (PEEK) commonly used in orthopedic implants are incapable of integrating with bone. Even for metals such as titanium alloys that are capable of integrating with bone, smooth surfaces provide for slow and poor integration. Moreover, integration surfaces on orthopedic implants that are adorned with teeth, spikes, grooves, and other projecting surfaces can actually impede or avoid bone integration.

Where integration is desired, the rate of integration directly relates to the overall well-being of the patient. The faster the integration, the faster the surgically repaired area heals, and the faster the patient can resume their lifestyle formerly impeded by the condition requiring orthopedic intervention. Accordingly, it is highly desired that integration occur between the orthopedic implant and adjacent bone. Therefore, there remains a need in the art for integration surfaces that can achieve rapid and high-quality osseointegration.

SUMMARY OF THE INVENTION

To meet this and other needs, and in view of its purposes, the invention features osteoinducting surfaces of an orthopedic implant, including bone-contacting and free surfaces. These osteoinducting surfaces are produced according to a process comprising additively manufacturing an orthopedic implant having one or more free surfaces and having one or more bone-contacting surfaces adapted to be placed in contact with bone, and then mechanically, chemically, or mechanically and chemically eroding the one or more bone-contacting surfaces, and, optionally mechanically, chemically, or mechanically and chemically eroding one or more of the one or more free surfaces, to remove alpha case and impart an osteoinducting roughness comprising micro-scale structures and nano-scale structures into the mechanically, chemically, or mechanically and chemically eroded surfaces. One or more of the one or more bone-contacting surfaces and free surfaces may comprise a macro-scale roughness. In preferred aspects, following the additive manufacturing, the process comprises mechanically eroding and then chemically eroding the one or more bone-contacting surfaces, and, optionally mechanically, chemically, or mechanically and chemically eroding one or more of the one or more free surfaces, to impart the osteoinducting roughness. Thus, in some preferred aspects where one or more of the one or more free surfaces are eroded, some of the free surfaces are eroded and some of the free surfaces are not eroded.

Bone-contacting surfaces and free surfaces produced according to this process significantly enhance, facilitate, and/or upregulate, including the rate and extent thereof, one or more of osteoinduction, osteogenesis, mesenchymal stem cell expression of alkaline phosphatase, preosteoblast expression of osterix, and osteoblast expression of osteocalcin. Such enhancement, facilitation, and/or upregulation occurs when such surfaces are brought in contact with bone or are brought in contact with mesenchymal stem cells. Such contact may be in vitro, or in vivo or in situ. The enhancement in one or more of osteoinduction, osteogenesis, mesenchymal stem cell expression of alkaline phosphatase, preosteoblast expression of osterix, and osteoblast expression of osteocalcin attained by surfaces produced according to this process is significantly greater than the osteoinduction, osteogenesis, mesenchymal stem cell expression of alkaline phosphatase, preosteoblast expression of osterix, and/or osteoblast expression of osteocalcin attained by other types of surfaces of orthopedic implants when such other types of surfaces are brought in contact with bone or are brought in contact with mesenchymal stem cells, which contact may be in vitro, or in vivo or in situ. In some aspects, such other types of surfaces are devoid of an osteoinducting roughness comprising micro-scale structures and nano-scale structures, for example, surfaces that have not been treated by mechanical and/or chemical erosion to impart an osteoinducting roughness comprising micro-scale structures and nano-scale structures.

In some aspects, the one or more bone-contacting surfaces produced according to the process, when placed in contact with bone, significantly enhance osteoinduction relative to the osteoinduction from a comparative bone-contacting surface comprising a macro-scale roughness and comprising an osteoinducting roughness comprising micro-scale structures and nano-scale structures produced by mechanically and chemically eroding a bulk substrate, when the comparative surface is placed in contact with bone. In some aspects, the one or more bone-contacting surfaces produced according to the process, when placed in contact with bone, significantly enhance osteogenesis relative to the osteogenesis from a comparative bone-contacting surface comprising a macro-scale roughness and comprising an osteoinducting roughness comprising micro-scale structures and nano-scale structures produced by mechanically and chemically eroding a bulk substrate, when the comparative surface is placed in contact with bone. In some aspects, the one or more bone-contacting surfaces produced according to the process, when placed in contact with bone, significantly enhance the level of expression of alkaline phosphatase by mesenchymal stem cells relative to the level of expression of alkaline phosphatase by mesenchymal stem cells from a comparative bone-contacting surface comprising a macro-scale roughness and comprising an osteoinducting roughness comprising micro-scale structures and nano-scale structures produced by mechanically and chemically eroding a bulk substrate, when the comparative surface is placed in contact with bone. In some aspects, the one or more bone-contacting surfaces produced according to the process, when placed in contact with bone, significantly enhance the level of expression of osterix by preosteoblasts relative to the level of expression of osterix by preosteoblasts from a comparative bone-contacting surface comprising a macro-scale roughness and comprising an osteoinducting roughness comprising micro-scale structures and nano-scale structures produced by mechanically and chemically eroding a bulk substrate, when the comparative surface is placed in contact with bone. In some aspects, the one or more bone-contacting surfaces produced according to the process, when placed in contact with bone, significantly enhance the level of expression of osteocalcin by osteoblasts relative to the level of expression of osteocalcin by osteoblasts from a comparative bone-contacting surface comprising a macro-scale roughness and comprising an osteoinducting roughness comprising micro-scale structures and nano-scale structures produced by mechanically and chemically eroding a bulk substrate, when the comparative surface is placed in contact with bone.

The step of additively manufacturing the orthopedic implant may comprise additively manufacturing the orthopedic implant with electron beam melting (EBM). The step of additively manufacturing the orthopedic implant may comprise additively manufacturing the orthopedic implant with selective laser sintering, including, for example, direct metal laser sintering (DMLS). The step of additively manufacturing the orthopedic implant may comprise additively manufacturing the orthopedic implant with selective laser melting, including, for example, laserCUSING™. The step of additively manufacturing the orthopedic implant may comprise additively manufacturing the orthopedic implant with fused deposition modeling (FDM), direct metal deposition, laser Engineered Net Shaping (LENS), wire-based directed energy deposition, or any other method using an energy source to melt. The additive manufacture process may further comprise hot isostatic pressing (HIP) or stress-relieving the orthopedic implant following the step of additively manufacturing the orthopedic implant.

The orthopedic implant preferably comprises a metal or ceramic. The metal may comprise a cobalt chromium alloy, an alloy of titanium, an alloy of titanium, aluminum, and vanadium, an alloy of titanium and nickel, nitinol, or stainless steel.

The invention also features orthopedic implants, which implants comprise one or more bone-contacting surfaces and one or more free surfaces that are produced according to any of the processes described or exemplified herein. Surfaces on these implants that are processed by mechanical erosion, chemical erosion, or both mechanical and chemical erosion include an osteoinducting roughness comprising micro-scale structures and nano-scale structures that significantly enhance, facilitate, and/or upregulate osteoinduction, including the rate and extent thereof, when such surfaces are brought in contact with bone or are brought in contact with mesenchymal stem cells, for example, following implantation of the implants within the body.

The invention still further features an orthopedic implant having a titanium or titanium alloy body with a plurality of surfaces. The orthopedic implant is produced according to a process comprising the steps of: (a) additively building the orthopedic implant; and then (b) mechanically, chemically, or mechanically and chemically eroding one or more surfaces of the orthopedic implant to (i) remove alpha case from, and (ii) impart an osteoinducting roughness including micro-scale structures and nano-scale structures into, the one or more surfaces. Alternatively, the process comprises the steps of (a) additively building the orthopedic implant having one or more free surfaces and having one or more bone-contacting surfaces adapted to be placed in contact with bone, at least the one or more bone-contacting surfaces having a macro-scale roughness that inhibits movement of the orthopedic implant when the bone-contacting surfaces are placed in contact with bone; and then (b) sequentially mechanically and chemically eroding one or more of the one or more free surfaces and the one or more bone-contacting surfaces to (i) remove alpha case from, and (ii) impart an osteoinducting roughness including micro-scale structures and nano-scale structures into, one or more of the one or more free surfaces and the one or more bone-contacting surfaces.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. Included in the drawing are several figures, as summarized below.

FIG. 7A is an optical micrograph of a metallographic section of a titanium disc off the EBM machine and subject to HIP;

FIG. 7B is an optical micrograph of a metallographic section of a titanium disc off the EBM machine and subject to both HIP and a conventional blast process;

FIG. 7C is an optical micrograph of a metallographic section of a titanium disc off the EBM machine and subject to both HIP and to mechanical and chemical erosion.

DETAILED DESCRIPTION OF THE INVENTION

Figure 1A:
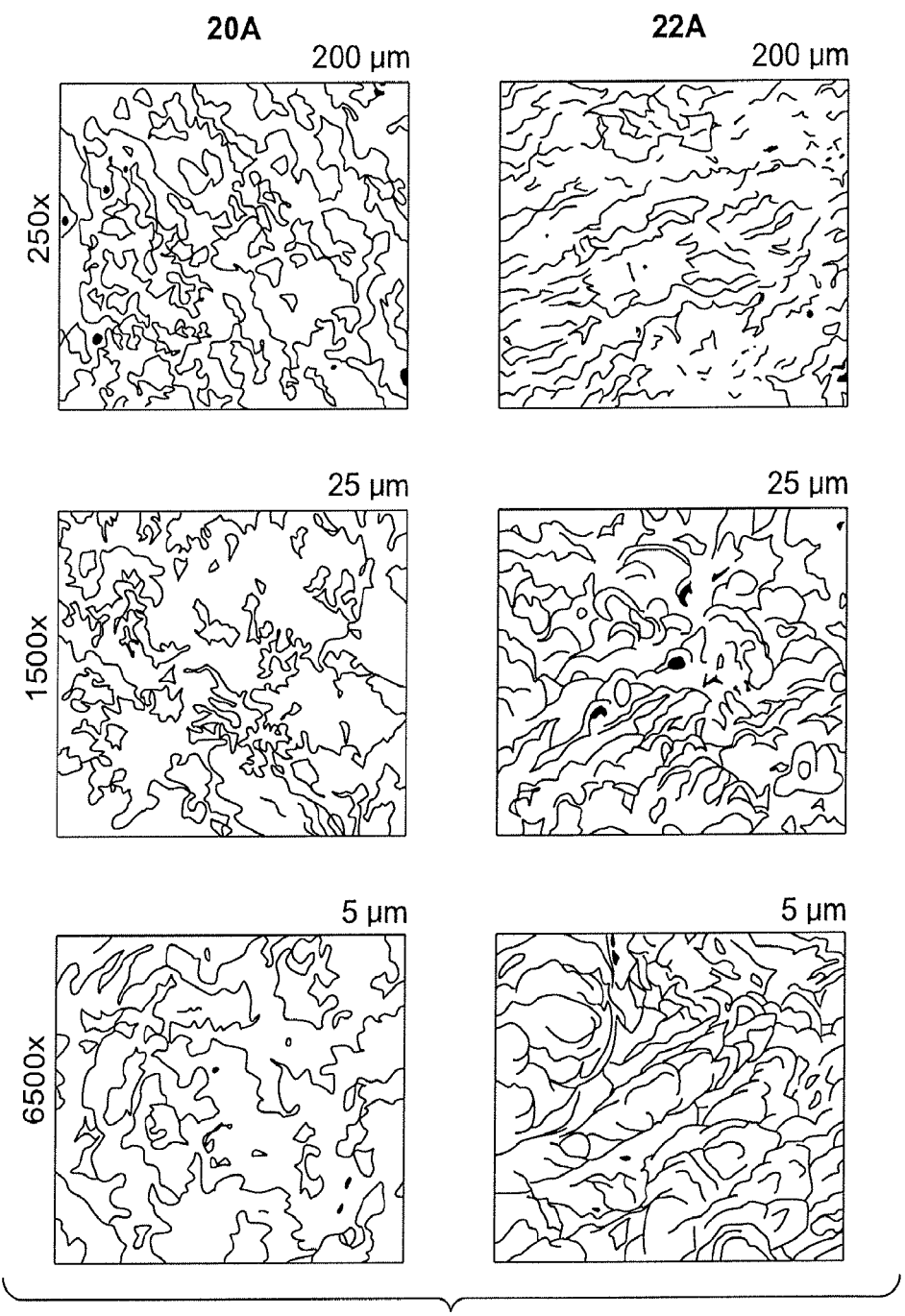
FIG. 1A shows scanning electron microscope (SEM) images of additively manufactured surfaces, including surface 20A which is a DMLS-produced surface that was subject to stress-relief but no erosion and surface 22A which is a DMLS-produced surface that was subject to stress-relief and mechanical and chemical erosion.
Figure 1B:
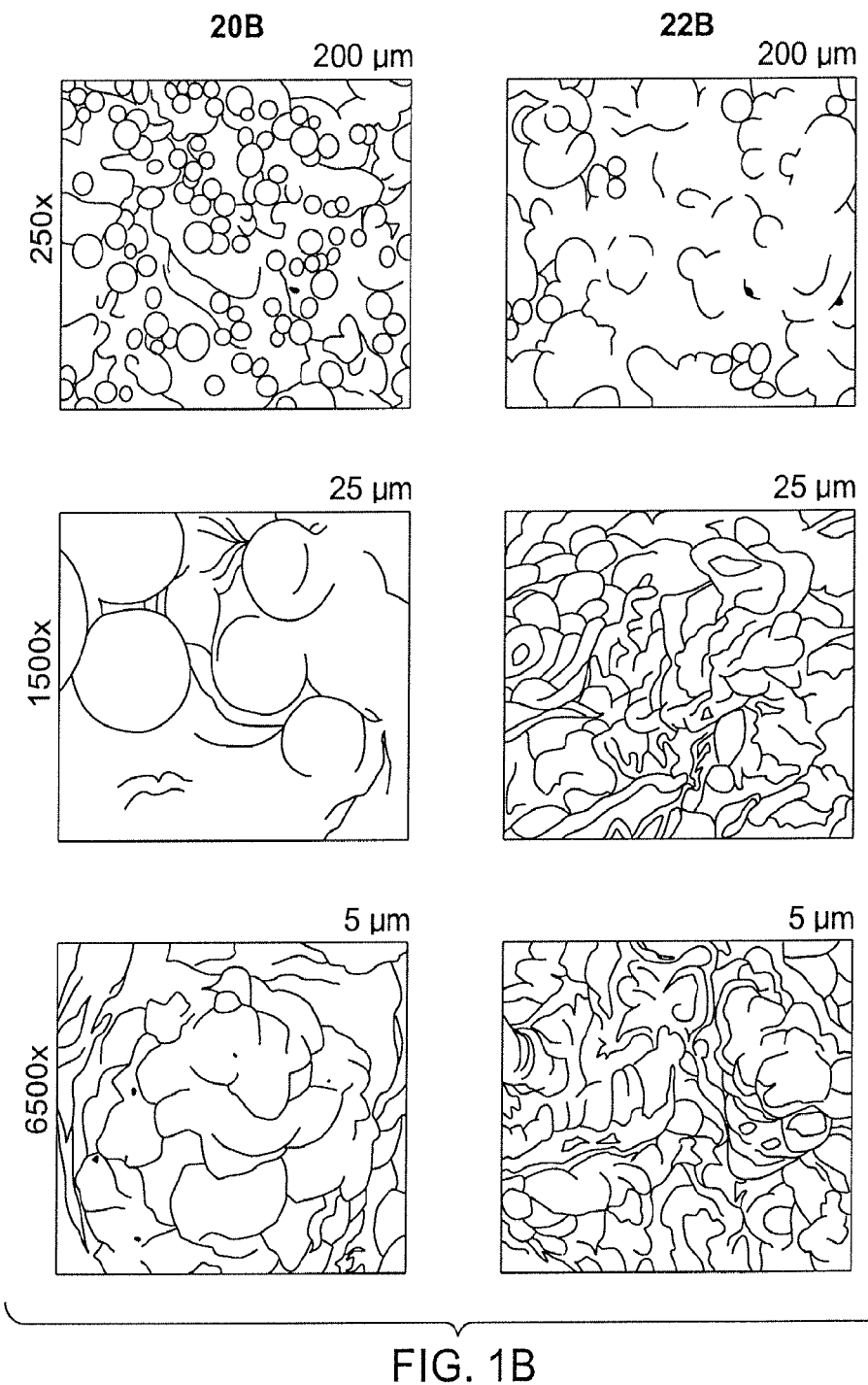
FIG. 1B shows SEM images of additively manufactured surfaces, including surface 20B which is an EBM-produced surface that was subject to hot isostatic pressing (HIP) but no erosion and surface 22B which is an EBM-produced surface that was subject to HIP and mechanical and chemical erosion.
Figure 1C:
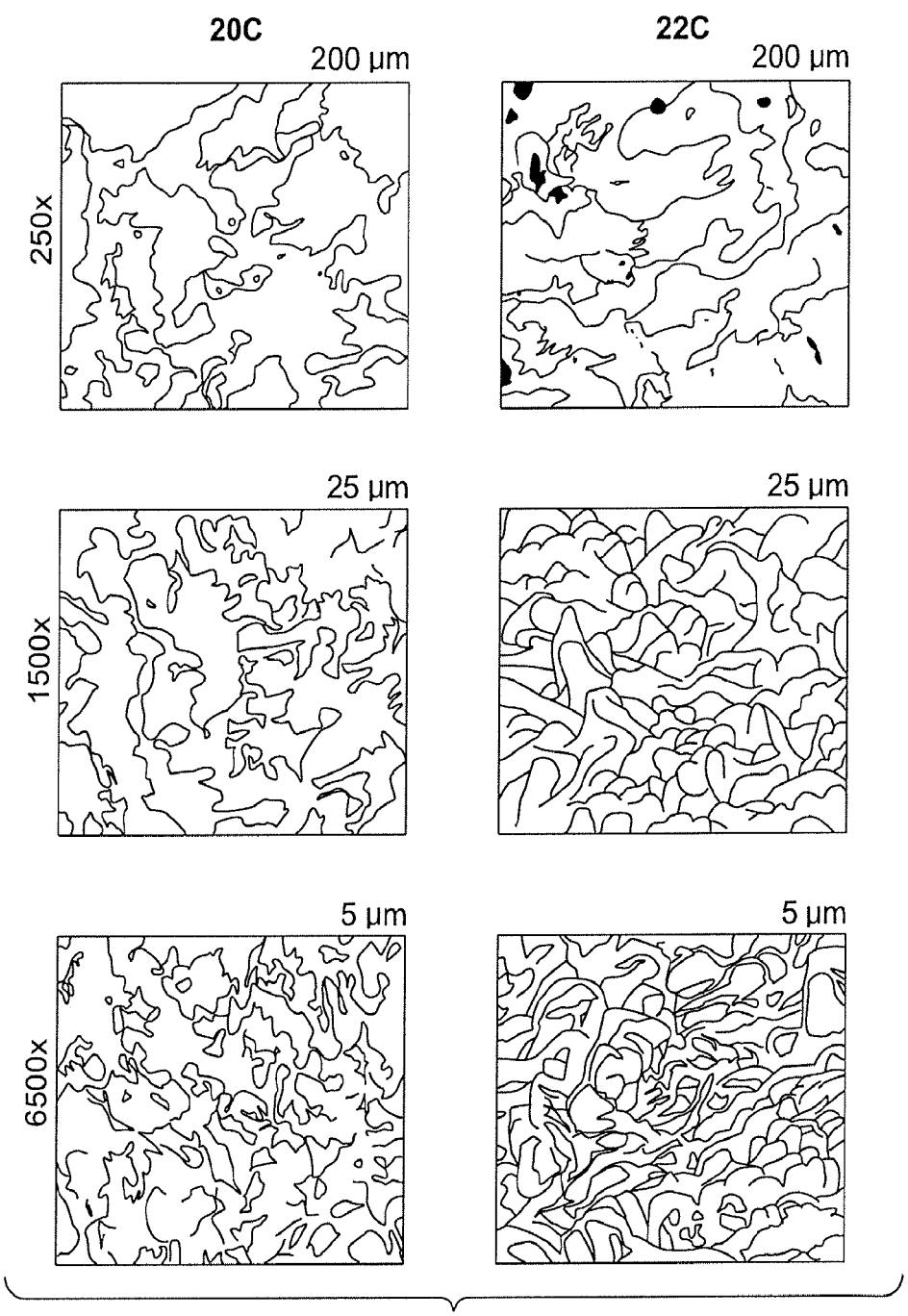
FIG. 1C shows SEM images of additively manufactured surfaces, including surface 20C which is a DMLS-produced surface that was subject to HIP but no erosion and surface 22C which is a DMLS-produced surface that was subject to HIP and mechanical and chemical erosion.
Figure 1D:
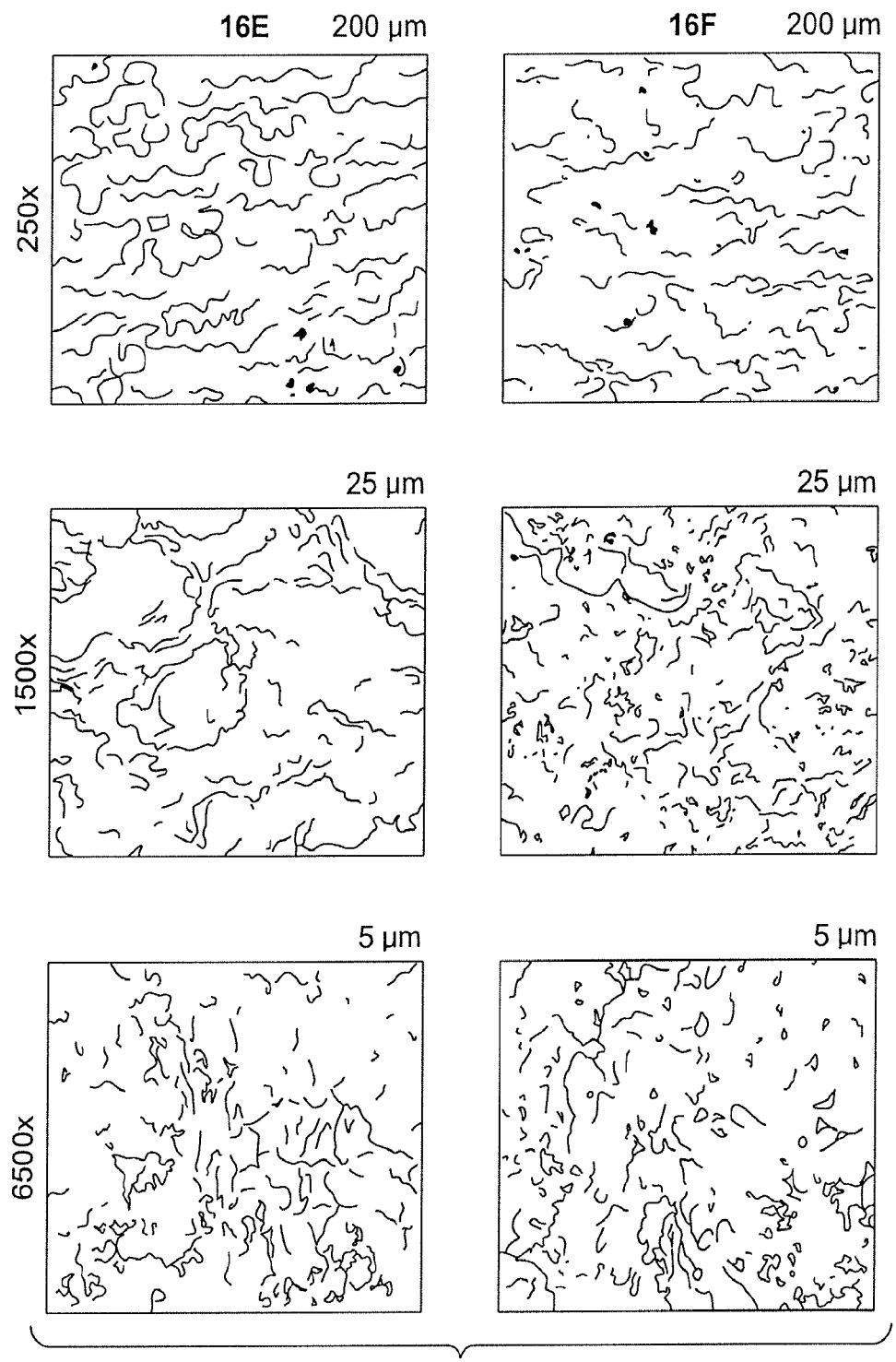
FIG. 1D shows SEM images of additively manufactured surfaces, including surface 16E which is a laser-produced surface that was subject to hot isostatic pressing and mechanical erosion using a sodium bicarbonate blast and surface 16F which is a laser-produced surface that was subject to hot isostatic pressing and mechanical erosion using a titanium blast.
Figure 1E:
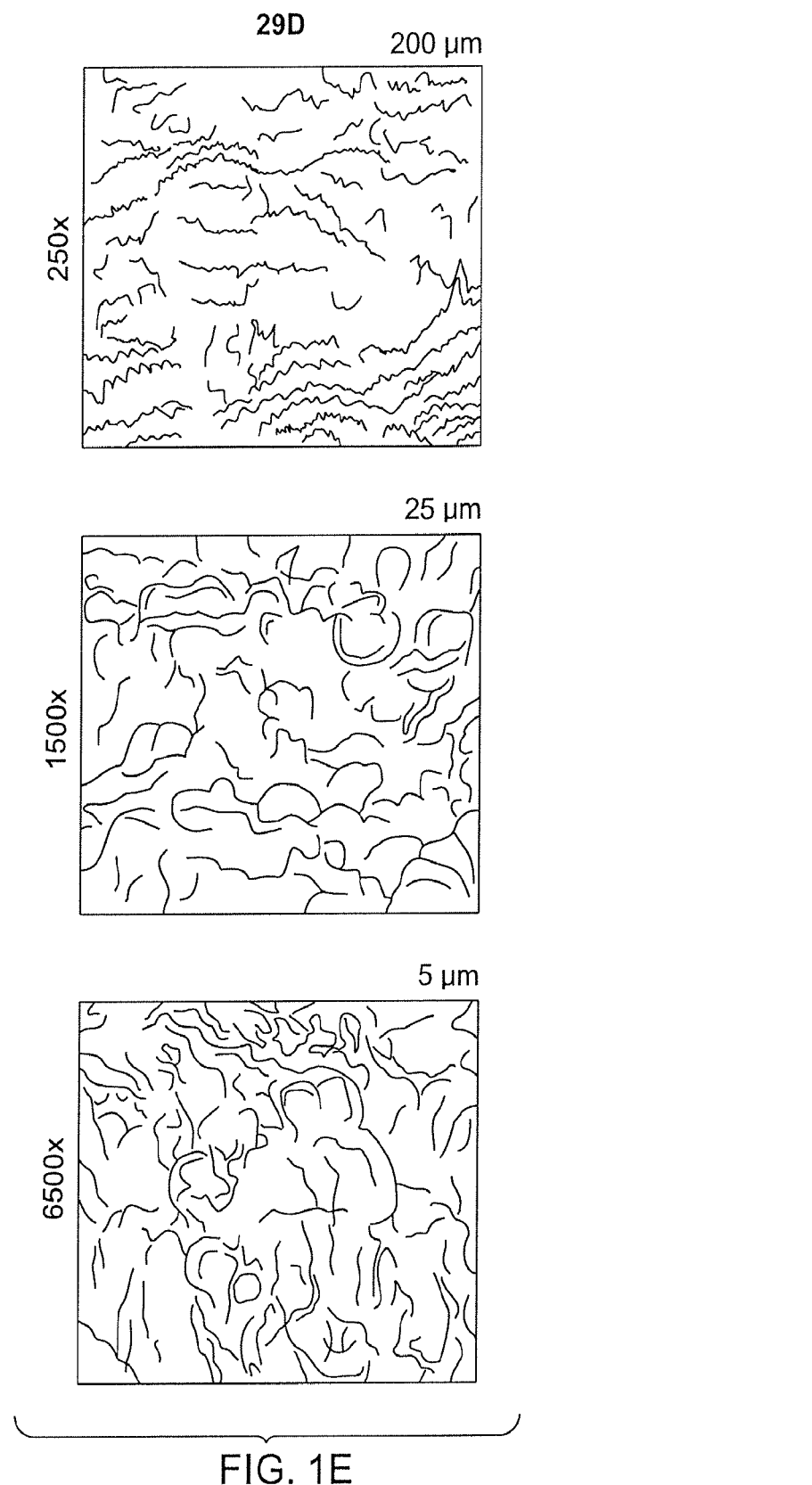
FIG. 1E shows SEM images of additively manufactured surface 29D, which is a laser-produced surface with a built-in macro texture that was subject to hot isostatic pressing and mechanical and chemical erosion.

Various terms relating to aspects of the present invention are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

The terms "subject" or "patient" are used interchangeably. A subject may be any animal, including mammals such as companion animals, laboratory animals, and non-human primates. Human beings are preferred.

"Vertically" additively manufacturing an orthopedic implant means that during the additive manufacture process, the build begins with a surface of the implant that does not contact bone (e.g., a free surface), such that the bone-contacting surfaces result from one or more of the edges of the additively-laid layers. By way of example, but not of limitation, if the top or bottom surfaces of an orthopedic implant are intended to contact bone but sides of the implant are not intended to contact bone, then the build begins with one of the sides of the implant, and the bone-contacting top and bottom arise as the layers are deposited. Vertical additive manufacture stands in contrast to the more traditional horizontal additive manufacturing processes where the build begins with a bone-contacting surface. By way of example, but not of limitation, if the top or bottom surfaces of an orthopedic implant are intended to contact bone but sides of the implant are not intended to contact bone, then with horizontal additive manufacturing, the build begins with either of the bone-contacting top or bottom layers.

As used herein, a "bulk substrate" means an orthopedic implant, or a precursor, exemplar, or archetype of an orthopedic implant such as a preform, blank, solid, cast of metal, wrought metal, block of metal, metal ingot, or bulk of metal, that is made without any additive manufacturing.

As used herein, "osteoinduction" and "osteoinducting" refers to the induction or initiation of osteogenesis, and includes the recruitment of immature mesenchymal stem cells to a processed (e.g., mechanically and/or chemically eroded) bone-contacting surface and/or to a processed (e.g., mechanically and/or chemically eroded) free surface of an orthopedic implant, followed by the phenotype progression and differentiation of these stem cells to a preosteoblast and the further phenotype progression and differentiation of a preosteoblast to an osteoblast. Such phenotype progression and differentiation are characterized by upregulation of alkaline phosphatase expression by the mesenchymal stem cells, followed by upregulation of osterix as the mesenchymal stem cell differentiates to a preosteoblast, and followed by upregulation of osteocalcin as the preosteoblast matures into an osteoblast.

"Osteogenesis" includes the formation and development of bone matrix.

As used herein, "free surfaces" are surfaces of orthopedic implants that do not directly contact bone at the time the implant is implanted within the body. Nevertheless, free surfaces that are processed to impart an osteoinducting roughness comprising micro-scale and nano-scale structures may stimulate de novo bone growth such that after a period of time following implantation and attendant bone growth out from the free surfaces, the free surfaces contact bone. In some aspects, one or more of the free surfaces of an orthopedic implant may contact a bone graft material (e.g., synthetic, allograft, or autograft material), for example, when the implant is implanted within the body. The practitioner may place a bone graft material in contact with one or more of the free surfaces.

It has been observed in accordance with the invention that additive manufacture of orthopedic implants followed by a combination of mechanical and chemical erosion of the additively manufactured surfaces results in such surfaces being able to stimulate preosteoblasts to mature into osteoblasts, and to stimulate preosteoblasts and osteoblasts to upregulate the expression of proteins that promote and support bone production. It was found that at least the amount of such proteins was significantly enhanced by these surfaces, and it is believed that the rate of the expression of such proteins was also enhanced. It is believed that these surfaces are also able to stimulate mesenchymal stem cells to differentiate into preosteoblasts, and to upregulate the expression of proteins that promote and support bone production.

Where integration of orthopedic implants with adjacent bone (e.g., osseointegration) is a desired outcome, the upregulation of such proteins means that the integration process in the body (e.g., between such surfaces and the adjacent bone) will proceed rapidly and robustly. Accordingly, the invention features osteoinducting bone-contacting surfaces for orthopedic implants that are produced according to a process that begins with additive manufacture of an orthopedic implant followed by treatment of the surfaces of the additively-produced implant that are intended to facilitate new bone growth with eroding techniques that produce and/or enhance osteoinducting structural features of the surfaces.

In general, the processes for producing osteoinduction-enhancing bone-contacting surfaces comprise first additively manufacturing an orthopedic implant, e.g., the implant body having the desired basic shape, configuration, and structural orientation for the particular location within the body where the implant is to be implanted and for the particular corrective application intended for the implant, and then treating one or more surfaces (e.g., either or both of bone-contacting and free surfaces) of the implant to remove alpha case and produce a bone growth-enhancing bioactive surface topography. In some preferred aspects, the one or more bone-contacting surfaces produced by sequential additive manufacturing and subtractive eroding processes comprise an overlapping macro-scale roughness, micro-scale roughness, and nano-scale roughness. In some preferred aspects, the one or more free surfaces produced by sequential additive manufacturing and subtractive eroding processes comprise an overlapping micro-scale roughness and nano-scale roughness. Each roughness may comprise regular, irregular, or combinations of regular and irregular structural features, e.g., the macro-scale roughness, micro-scale roughness, and nano-scale roughness may independently be regular, irregular, or both regular and irregular in terms of the structural arrangement of the surface.

Additive manufacturing processes produce surfaces that are generally microscopically smooth. Accordingly, it is preferred that the additive manufacturing techniques used to produce the orthopedic implant impart a macro-scale roughness in at least the bone-contacting surfaces, although free surfaces produced via the additive process may be rough or smooth to the touch. The macro-scale roughness comprises macro-scale structural features, which function to grip bone and inhibit movement of an implant once implanted within the body. The shape, configuration, orientation, size, design and layout of the macro-scale features may be programmed into the additive manufacture software.

Thus, in some aspects, the additive manufacturing of the orthopedic implant includes the engineering and designing of the geometry, dimensions, and structural features of the implant body, via additive manufacture. The implant body may comprise any suitable shape or geometry, and any suitable number of sides and surfaces—including bone-contacting surfaces and including free surfaces—which may depend, for example, on the particular shape and location of the site of implantation within the body. The implant may comprise flat, round, regular, and/or irregular surfaces. By way of example, but not of limitation, the orthopedic implant may comprise a joint replacement (e.g., hip, knee, shoulder, elbow, ankle, wrist, jaw, etc.), a long or short bone (or portion thereof) replacement, a skull or jaw bone replacement, an implant intended to induce fusion or physical joining of separate bones (e.g., finger joints, ankle joints, vertebrae, or spinal motion segment), an implant intended to fasten another implant to a bone (e.g., bone screws, pedicle screws, and fixation elements), an implant to facilitate rejoinder of broken bones, including bone screws, intramedullary nail, rods, and plates, etc., or any implant to replace, repair, brace, or supplement any bone in the body. In some aspects, the implant comprises an implant for replacing an intervertebral disc, or for replacing a spinal motion segment. In highly preferred aspects, the implant is intended for integration with the surrounding bone. Implant engineering and design may be computer assisted.

In addition, the additive manufacturing also includes the engineering and designing of the geometry, dimensions, and structural features of the macro-scale structural features or roughness to be imparted into the bone-contacting surfaces of the implant. The engineering may derive from the imaging/optical scanning of a macro-scale roughness from surfaces produced by aggressively acid-etching a bulk substrate, with the imaged information imported into the additive manufacture program model.

The engineering of the macro-scale roughness may take into account rational design of particular values for one or more of the roughness parameters established by the International Organization for Standardization (ISO), e.g., ISO 468:1982. Such parameters include, but are not limited to, Rp (max height profile), Rv (max profile valley depth), Rz (max height of the profile), Rc (mean height of the profile), Rt (total height of the profile), Ra (arithmetic mean deviation of the profile), Rq (root mean square deviation of the profile), Rsk (skewness of the profile), Rku (kurtosis of the profile), RSm (mean width of the profile), RΔq (Root mean square slope of the profile), Rmr (material ratio of the profile), Rδc (profile section height difference), Ip (sampling length—primary profile), Iw (sampling length—waviness profile), Ir (sampling length—roughness profile), In (evaluation length), Z(x) (ordinate value), dZ/dX (local slope), Zp (profile peak height), Zv (profile valley depth), Zt (profile element height), Xs (profile element width), and Ml (material length of profile). Other parameters may include Rsa (surface area increase), Rpc (peak counts), H (Swedish height), ISO flatness (areal flatness deviation), Pt ISO (peak-to-valley profile height), Rtm (mean peak-to-valley roughness), Rv (lowest value), Rvm (mean valley profile depth), Ry (maximum peak-to-valley roughness), Rpm (mean peak areal height), S (average spacing between local peaks), SM (average spacing between peaks at the mean line), summit number, summit density, summit spacing, valley number, valley density, and valley spacing. Additionally, it is contemplated that the additive manufacturing may further include the engineering and designing of the geometry, dimensions, and structural features of the micro-scale roughness and/or the nano-scale roughness to be imparted into the bone-contacting or free surfaces of the implant, particularly as the capabilities of additive manufacturing equipment evolve to allow for finer and more nuanced details to be additively manufactured.

The orthopedic implants may be additively manufactured from any suitable material, including a metal, a ceramic, bone, or any combination or composite thereof. Metals are highly preferred. Metals may comprise an alloy. Preferred metals include titanium and titanium alloys such as nickel-titanium alloys (for example, nitinol), and aluminum and vanadium (e.g., 6-4) alloys of titanium, cobalt chromium alloys, as well as surgical grade steel (e.g., stainless steel). The orthopedic implants are preferably not manufactured from polymers such as polyether ether ketone (PEEK).

Additive manufacturing may comprise successively layering by depositing solid material onto a substrate, then sintering or melting the deposited solid material into a layer of the orthopedic implant, then depositing more solid material onto the previous layer, then sintering or melting the newly deposited layer to both fuse with the previous layer and establish the next layer, and repeating these steps until the implant is completed. The solid material being deposited may be in the form of wires, powders, particles, granules, fragments, or combinations thereof, which is sintered or melted by an energy source. The powders, particles, granules, fragments, or combinations thereof preferably are substantially spherical in shape. It is preferred that the powders, particles, granules, fragments, or combinations thereof do not comprise irregular shapes or edges, or jagged edges. The spheres may comprise different sizes, or may be substantially the same size.

The additive manufacturing may comprise sintering and/or melting of the powders, particles, granules, wires, fragments, or combinations thereof. The sintering and/or melting preferably achieves substantially complete melting of the powders, particles, granules, fragments, or combinations thereof such that the layer being deposited is comprised of substantially fully molten material, the material preferably being metal. Suitable additive manufacturing techniques include, without limitation, selective laser sintering, including, for example, direct metal laser sintering (DMLS) (DMLS® is a service mark of EOS GmbH), selective laser melting, including, for example, laserCUSING™ (Concept Laser Schutzrechtsverwaltungs GmbH), electron beam melting (EBM), fused deposition modeling (FDM), direct metal deposition, laser Engineered Net Shaping (LENS), and wire-based directed energy deposition. Thus, the energy source may comprise a laser or an electron beam, although any suitable technique for melting the material may be used.

Deposition and/or sintering or melting may take place in an inert environment, for example, with low oxygen and/or in the presence of nitrogen and/or argon. In some aspects, a preceding layer (having just been formed) has not substantially solidified prior to the successive layer being deposited thereon. In some aspects, a preceding layer (having just been formed) has at least partially solidified prior to the successive layer being deposited thereon.

In some aspects, the implant is vertically additively manufactured. The vertical additive manufacture begins by creating a layer that would constitute a surface other than a bone-contacting surface of the implant being manufactured (e.g., a free surface), with successive layers being deposited and sintered or melted until the opposing face is completed. Bone-contacting surfaces thereby arise from the edges of the layers laid in a vertical build scheme.

Following completion of building the implant body through the additive process, the implant body may be subject to stress-relieving processing, including a reheat of the formed implant body. Stress relief may be carried out under vacuum and/or an inert gas. The heating may occur at temperatures that cause diffusion within the metal, and then followed by a cooling step. In some aspects, the reheat may also be accompanied by pressure. The pressure may be either uniaxial (e.g., applied from one direction; hot uniaxial pressing or HUP) or isostatic (e.g., applied evenly from all directions). Hot isostatic pressing (HIP) is highly preferred.

HIP is conducted by placing the implant body in a sealed container which can be heated and pressure controlled by adding and removing gases. Typically, once the implant body is placed in the sealed container, the container is evacuated to remove any contaminating gasses. The container is then heated while introducing an inert gas (for example, Argon) into the chamber to increase the pressure. The container is then held at the elevated temperature and pressure for a period of time, after which the container is rapidly cooled and depressurized.

HIP is conducted at a temperature below the melting point of the material from which the implant body is made, but at a sufficiently high temperature where diffusion and plastic deformation of the implant body occur. The temperature is typically less than 80% of the melting temperature. For example, for a titanium alloy including 6% aluminum and 4% vanadium, the implant body may be heated to a temperature ranging from 895° C. (1,643° F.) to 955° C. (1,751° F.)±15° C. (59° F.) at a pressure of at least 100 MPa (14,504 PSI) for a period of 180±60 minutes and then cooled to below 425° C. (797° F.), according to ASTM Standard Specification F3001. Similar specifications are known to one of ordinary skill in the art for other materials, for example other standards from ASTM.

It is believed that HIP results in changes to the implant body. For example, the combination of temperature and pressure results in the collapse of any inclusions present within the implant body. In some aspects, the density of the implant body may be substantially near or equal to 100% following HIP, meaning that the implant may be substantially free of inclusion bodies (internal pores). Removing inter-layer boundaries and removing inclusions improve the mechanical strength of the implant body and reduce the likelihood of failure once implanted. Metal diffusion may also reduce or eliminate boundaries between metal layers resulting from the additive manufacturing process described above.

In addition, the elevated temperature and pressure from HIP encourages metal diffusion across grain boundaries, resulting in a refinement of the grain structure, grain size, grain composition, grain distribution, or any combination thereof. In some aspects, HIP may increase at least the grain size, particularly when coupled to an electron beam melting additive build. HIP may change both the grain structure and the intergranular boundaries on the implant surfaces.

Following the additive manufacturing steps, and further following stress-relief, HUP, or HIP treatments, if such treatments are employed in the process, the process further includes eroding the bone-contacting surfaces, the free surfaces, or both the bone-contacting and free surfaces that were additively produced to impart osteoinducting structural features into these surfaces. The osteoinducting structural features include micro-scale structures and nano-scale structures that promote or enhance osteoinduction. One or more of the bone-contacting surfaces of the additively manufactured implant are mechanically, chemically, or mechanically and chemically eroded to impart an osteoinducting roughness comprising micro-scale structures and nano-scale structures into the bone-contacting surfaces. In some aspects, one or more of the free surfaces of the additively manufactured implant are mechanically, chemically, or mechanically and chemically eroded to impart an osteoinducting roughness comprising micro-scale structures and nano-scale structures into the free surfaces. Thus, either or both of bone-contacting and free surfaces of the additively manufactured implant may be processed to comprise osteoinducting micro-scale and nano-scale structures. Effectively, such processing may establish an overlap of the macro-scale structures that were additively manufactured with the erosion-produced micro-scale and nano-scale structures.

The mechanical and/or chemical treatments serve as a subtractive process, for example, erosion or etching. Mechanical erosion includes, but is not limited to, exposure of bone-contacting surfaces of the orthopedic implant to photo etching, energy bombardment, plasma etching, laser etching, electrochemical etching, machining, drilling, grinding, peening, abrasive blasting (e.g., sand or grit blasting, including blasting with aluminum or titanium oxide particles), or any combinations of such processes. Chemical erosion may comprise, for example, exposure of select surfaces or the entire implant to a chemical such as an acid or a base, with the acid or base etching the bone-contacting surfaces that come in contact with the acid or base. Chemical erosion may include, but is not limited to, chemical, electrochemical, photochemical, photoelectrochemical, or other types of chemical milling, etching, or other treatments used to remove portions of the substrate. Etchants may be wet or dry, and any state: liquid, gas, or solid. In preferred aspects, mechanical erosion and chemical (e.g., acid) erosion are used successively following additive manufacturing. It is preferred that mechanical erosion precedes the chemical erosion. Preferably, neither mechanical erosion nor chemical erosion introduces pores into the bone-contacting surfaces.

Prior to erosion of implant surfaces for imparting osteoinducting features into such surfaces, other surfaces of the implant that are not intended to be osteoinducting or otherwise induce bone growth, or which have been additively manufactured as smooth, may be protected by masking. In some aspects, free surfaces may be protected by masking. The exposed, non-masked surfaces of the implant may then be mechanically and chemically eroded.

Mechanical erosion is preferably achieved by blasting using particles. Particles may include organic or inorganic media. Suitable particles include, for example, aluminum oxide particles and/or titanium oxide particles and/or glass bead particles and/or pumice particles and/or silicon carbide particles and/or hydroxyapatite particles, or other suitable metal particles, or ceramic particles. Organic particles such as walnut shells or dissolvable particles such as sodium bicarbonate are also suitable.

Chemical erosion is preferably achieved using acids, although any chemicals capable of eroding a bone-contacting surface of the implant materials may be used. Preferred acids are strong acids such as HF, $HNO_3$, $H_2SO_4$, HCl, HBr, HI, $HClO_4$, citric acid, and any combination thereof, although the particular acid used is not critical. It is believed that the acids etch the grain structures and grain boundaries in a way that enhances the osteoinduction-enhancing properties of the bone-contacting or free surfaces. It is highly preferred that the chemical erosion follows the mechanical erosion. Chemical erosion may be completed in a single chemical treatment, although multiple treatments may be employed in order to add or enhance the nano-scale structures on the bone-contacting surfaces. Control of the strength of the chemical erodent, the temperature at which the erosion takes place, and the time allotted for the erosion process allows fine control over the resulting surface produced by erosion.

One or both of the mechanical and chemical erosion processing steps might remove unwanted contaminants. In some applications, oxides that tend to form on metal surfaces can be removed. In other applications, however, oxides may be desirable and, therefore, the processing steps should be designed to avoid removing the oxides. More specifically, some oxide on titanium surfaces can be beneficial. See, for example, U.S. Patent Application Publication No. 2010/0174382 filed by Gretzer et al. Gretzer et al. disclose a bone tissue implant having an implant surface. The surface is covered by an oxide layer that includes strontium ions. The applicants assert that the strontium ions in the oxide layer have a desired osseoinductive effect.

In other applications, oxide on titanium surfaces must be avoided or removed. It is especially desirable to avoid or remove a specific oxygen-enriched surface phase called "alpha case" on implants formed of titanium or titanium alloys. One or a combination of the mechanical and chemical erosion processing steps discussed above may substantially remove alpha case, if present, from the eroded surfaces of a titanium implant. A discussion of such removal follows.

A. Alpha Case and its Titanium Basis

Titanium was discovered and named in 1791 and 1795, respectively. Although its impure form was first prepared in 1887, the pure metal (99.9%) was not made until 1910. Titanium is found in a number of sources including meteorites, minerals, iron ores, the ash of coal, plants, and the human body. The method that is still largely used to produce titanium commercially was discovered in 1946 and uses magnesium to reduce titanium tetrachloride and isolate the pure metal.

Pure titanium is a lustrous, white metal. It has a relatively high melting point of about 1,720° C. (3,140° F.), a low specific gravity of 4.5, a low density, good strength, and excellent resistance to corrosion at temperatures below about 425-540° C. (800-1,000° F.). The modulus of elasticity of titanium is $16 \times 10^6$ $lb/in^2$, which means that it has greater stiffness than most aluminum alloys. Titanium is easily fabricated. These properties make the use of titanium and its alloys very attractive, and titanium is important as an alloying agent with other metals. Alloys of titanium are used, for example, in medical implants.

Titanium metal and its alloys have the disadvantage of reacting with other elements at temperatures above about 425° C. (800° F.), which restricts its use at elevated temperatures. The reaction characteristics of titanium at elevated temperatures cause considerable difficulties in processing operations as well as in its initial production.

Titanium exists in two allotropic forms: alpha at temperatures up to 885° C. (1,625° F.) and beta above that temperature. Alpha titanium has an hexagonal close packed (HCP) crystal structure while beta is body-centered cubic (BCC). Most alloying elements decrease the alpha-to-beta transformation temperature. Oxygen, nitrogen, and aluminum raise the transformation temperature. Oxygen and nitrogen increase hardness and strength, however, with a decrease in ductility and, hence, formability. The stabilizing effect of aluminum on the alpha phase promotes stability at higher temperatures, which makes aluminum an important element in many of the titanium alloys.

The alloying elements iron, manganese, chromium, molybdenum, vanadium, columbium, and tantalum stabilize the beta phase, thus decreasing the alpha-beta transformation temperature. Additions of columbium and tantalum produce improved strength and help in preventing the embrittlement produced by the presence of compounds of titanium and aluminum. The elements nickel, copper, and silicon are active eutectoid-formers, while manganese, chromium, and iron are sluggish in the formation of a eutectoid. The elements tin and zirconium are soluble in both the alpha and beta structures.

Titanium alloys can be classified into three general categories depending upon the structures: (1) all-alpha alloys contain neutral alloying elements and/or alpha stabilizers only, are not responsive to heat treatment, and, hence, do not develop the strength possible in other alloys; (2) alpha-beta alloys contain a combination of alpha and beta stabilizers, are heat treatable to various degrees, and have good ductility; and (3) all-beta alloys are metastable, have relatively low ductility, contain sufficient beta stabilizers to completely retain the beta phase upon processing, and can be solution treated and aged to achieve significant increases in strength.

Figure 4:
FIG. 4 shows the titanium microstructure, illustrating the different alloy phases of titanium.

FIG. 4 shows an example of the titanium microstructure illustrating the different alloy phases of titanium. Stabilizers are elements that have high solubility in metals and are typically used in alloys. The purpose of adding stabilizers to titanium is to alter the transformation temperature of a specific phase to create a binary alpha-beta phase. Alpha stabilizers, typically aluminum, are added to raise the transformation temperature of the alpha phase. Vanadium, an isomorphous beta stabilizer, is completely soluble in the beta phase. Other beta stabilizers such as iron are not completely soluble, which produces eutectoid phase. The stabilizers are represented in the name by their periodic table symbols and weight percent. For example, Ti-6Al-4V is 6% aluminum and 4% vanadium.

Ti-6Al-4V is the most common titanium alloy and accounts for more than 50% of total titanium usage. It is an alpha-beta alloy, which is heat treatable to achieve moderate increases in strength. Ti-6Al-4V is a world standard in many applications because it offers high strength, light weight, ductility, and corrosion resistance. One of the most common applications of this alloy is medical devices.

ELI stands for extra low interstitials and is a higher-purity version of Ti-6Al-4V, with lower limits on iron and interstitial elements carbon and oxygen. Like Ti-6Al-4V, it is also an alpha-beta alloy. TI-6Al-4V ELI has excellent biocompatibility, and therefore has been the material of choice for many medical applications. It has superior damage tolerance (fracture toughness, fatigue crack growth rate) and better mechanical properties at cryogenic temperatures when compared to standard Ti-6Al-4V. Common applications for TI-6-4 ELI include joint replacements, bone fixation devices, surgical clips, and cryogenic vessels.

B. Alpha Case

Titanium readily absorbs oxygen at high temperatures. When titanium and its alloys are exposed to heated air or oxygen, the formation of the oxygen-enriched surface phase called alpha case can occur. The alpha case layer is caused by oxygen diffusion into the titanium surface. More generally, alpha case is the carbon, nitrogen, or especially oxygen-enriched alpha stabilized surface that is present on titanium after heating.

Figure 5:
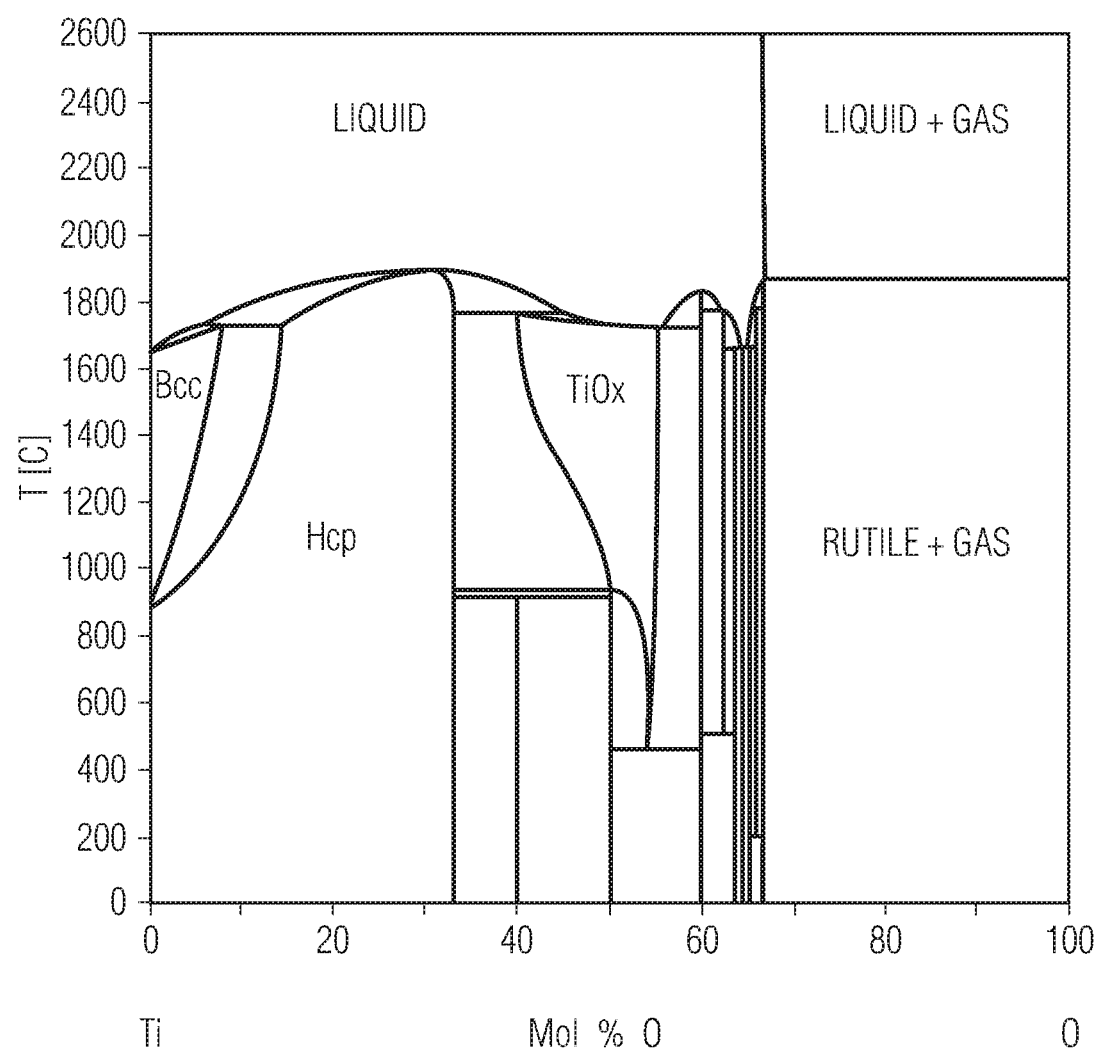
FIG. 5 represents a titanium-oxygen phase diagram.

FIG. 5 represents a titanium-oxygen phase diagram. The HCP phase represents the alpha phase and BCC is the beta phase. The alpha-beta phase is the region between HCP and BCC. The line dividing the binary phase from the HCP phase is the concentration of oxygen needed to form alpha case. Often, heat treatment processes reach temperatures on the phase diagram where this scenario is possible.

Figure 6:
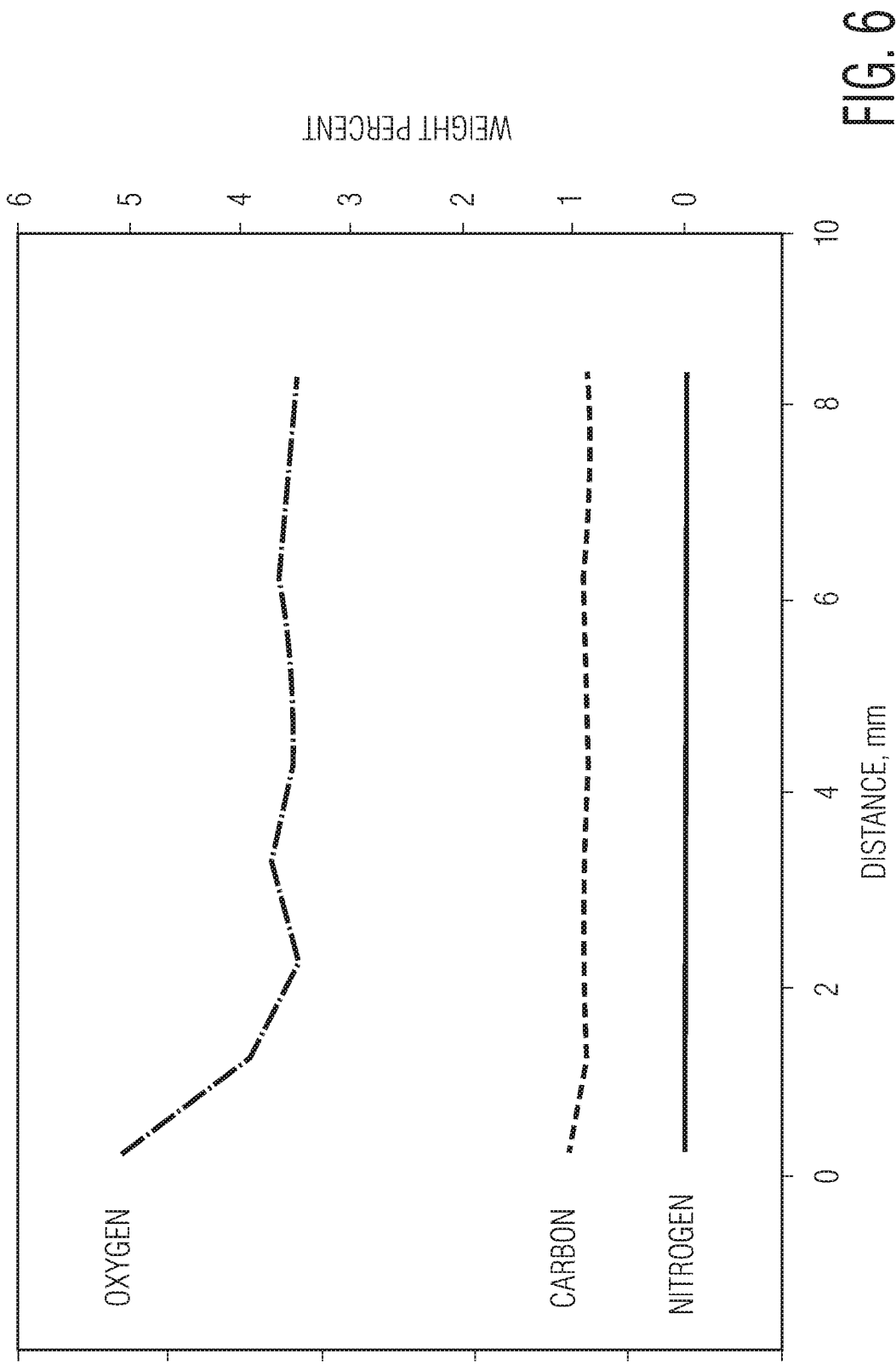
FIG. 6 is a graph representing carbon, nitrogen, and oxygen concentrations as a function of distance from the surface when air reacts with titanium during a heating process.

FIG. 6 is a graph representing carbon, nitrogen, and oxygen concentrations as air reacts with titanium at the titanium surface during a heating process. As expected, the carbon and nitrogen concentrations are low and stable. The oxygen is much more soluble in titanium; therefore, its concentration gradient is much higher at the surface. The values presented in the graph of FIG. 6 are subject to heating conditions, but the general behavior of oxygen, nitrogen, and carbon is typical for titanium. The oxygen concentration gradient represents the alpha case phase described above. The thickness of the alpha case depends on the exposure time, atmosphere, and temperature.

Alpha case is undesirable because it is hard and brittle. Further, alpha case tends to create a series of micro-cracks which degrade the performance of the titanium metal and, especially, its fatigue strength properties. Alpha case still further presents drawbacks against titanium usage because alpha case can affect adversely corrosion resistance, and limits the high temperature capability of titanium with respect to mechanical properties.

C. Forming Surfaces Free of Alpha Case

Given the disadvantages of alpha case, it is often desirable to form surfaces of titanium implants that are free of alpha case. Generally, there are two ways to achieve such surfaces. One way is to avoid or at least minimize the formation of alpha case in the first place (i.e., during processing of the titanium). Formation of alpha case can be minimized by using vacuum metallurgy or an inert gas in which the titanium is heated in the absence of oxygen. Thus, alpha case can be minimized or avoided by processing titanium at very deep vacuum levels or in inert environments. For a variety of reasons, however, it may be impractical or undesirable to process titanium in the absence of oxygen.

It is also possible to apply a coating to block carbon, nitrogen, and oxygen from the titanium surfaces being heated to control the formation of alpha case. The Ceram-Guard® line of coatings available from A.O. Smith Corporation may be suitable. The Ceram-Guard® coatings are high-temperature ceramic frits for temporarily coating and protecting metal during heating. If no alpha case forms on the titanium surfaces, then there is no need to remove it.

Once present on the surface of titanium, however, the second way to form surfaces of titanium implants that are free of alpha case is to remove the alpha case. Alpha case can be removed after heat treatment mechanically or chemically. See, for example, European Patent Application Publication No. 1947217 B1, titled "Method of removing an alpha-case titanium layer from a beta-phase titanium alloy," published on May 23, 2012 and assigned to United Technologies Corporation. The published application discloses a method of surface treating a titanium article that includes the step of chemically removing a surface layer having titanium alloy alpha-phase. In one disclosed example, the chemical removal includes using a first solution having nitric acid and hydrofluoric acid, and a second solution having nitric acid.

An emerging technique is to subject the titanium metal to an electrochemical treatment in molten salts, such as calcium chloride or lithium chloride at elevated temperatures. This method is effective, at least in laboratory settings, in removal of the dissolved oxygen from the alpha case, and hence recovery of the metal. Unfortunately, however, an unwanted consequence of the high temperature treatment is the growth of the grains in the metal. Grain growth may be limited by lowering the molten salt temperature. Alternatively, the metal may be further processed to break the large grains into smaller ones.

An important aspect of the processes used to form implant surfaces that enhance osteoinduction, according to the present invention and when the implant is formed of titanium, is to remove any alpha case. The alpha case is removed by the subtractive processing steps of mechanical erosion (e.g., machining), chemical erosion (e.g., etching or milling), or both. These steps are discussed above. The efficacy of such subtractive processing steps in removing alpha case is illustrated in FIGS. 7A, 7B, and 7C.

Alpha case is visible in a polished and etched microsection as a white layer in an optical metallurgical microscope or a dark layer in a scanning electron microscope (SEM) in back-scatter mode. (A SEM is a type of microscope that produces images of a sample by scanning it with a focused beam of electrons.) Alpha case can also be detected by micro-hardness indentation of a section normal to the surface.

Titanium discs were additively manufactured using electron beam melting (EBM). These discs were then subject to hot isostatic pressing (HIP). One of the discs received no further processing (FIG. 7A), another disc was blasted using a conventional process (FIG. 7B), and yet another disc was subject to mechanical and chemical erosion according to the process steps discussed above. Optical micrographs of the discs were obtained, and are shown in FIGS. 7A, 7B, and 7C.

FIG. 7A is an optical micrograph of a metallographic section of a titanium disc off the EBM machine and subject to HIP. The disc exhibited a lighter etching phase (area between two arrows) consistent with the presence of alpha case, approximately 0.09 mm deep. FIG. 7B is an optical micrograph of a metallographic section of a titanium disc off the EBM machine and subject to both HIP and a conventional blast process. The disc exhibited a lighter etching phase (area between two arrows) consistent with the presence of alpha case, approximately 0.015 mm deep. FIG. 7C is an optical micrograph of a metallographic section of a titanium disc off the EBM machine and subject to both HIP and to mechanical and chemical erosion according to the process steps discussed above. The disc did not exhibit any lighter etching phase, indicating the absence of any alpha case.

Mechanical erosion, chemical erosion, and the combination of mechanical and chemical erosion substantially removes alpha case, if present, from the eroded surfaces of the titanium implant. It is believed that this erosion combination fully removes alpha case. Thus, bone-contacting and free surfaces of the implant are preferably substantially free or completely free of alpha case in some aspects.

Figure 8:
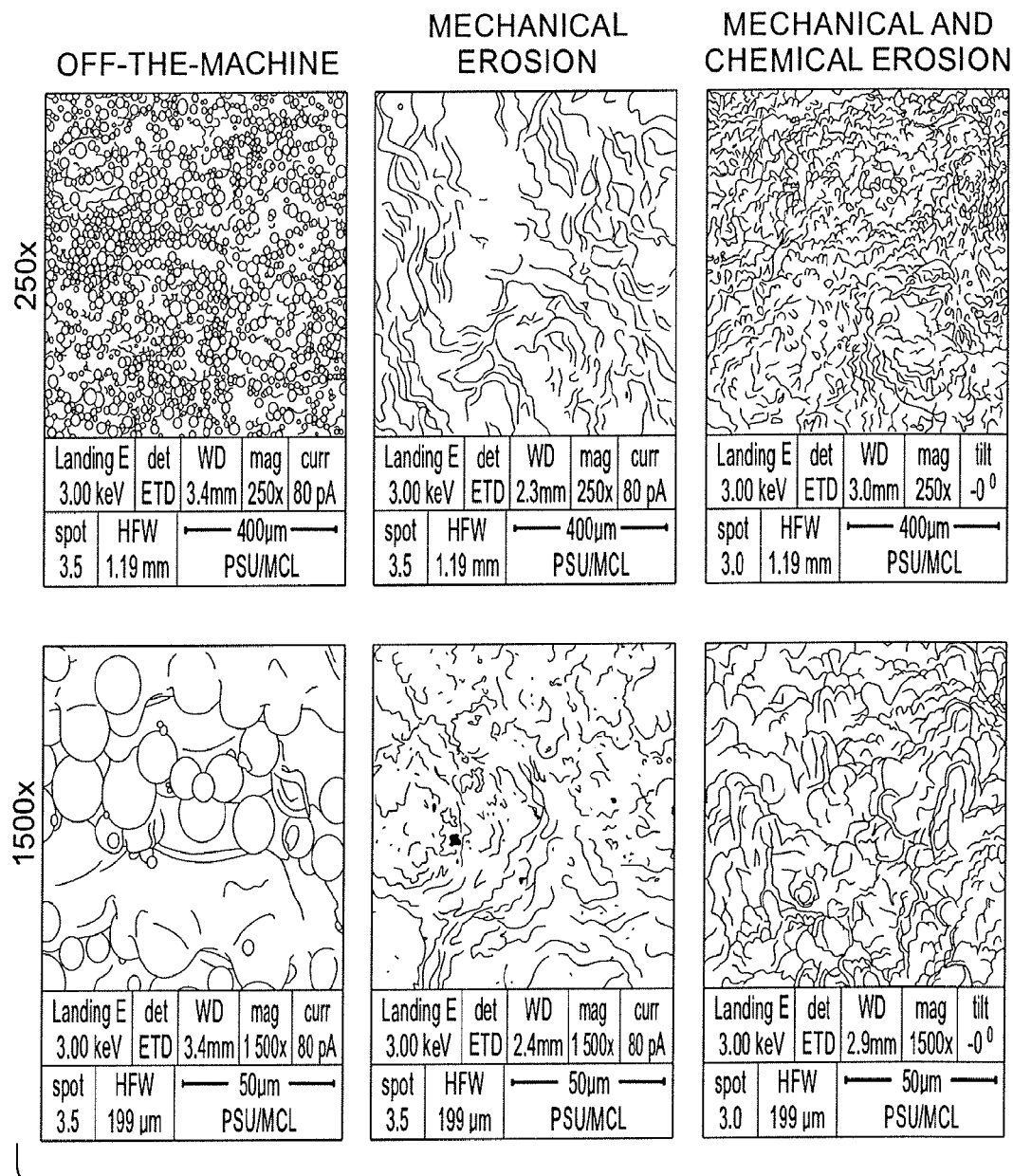
FIG. 8 shows how mechanical erosion and the combination of mechanical and chemical erosion can remove unsintered or partially sintered powder from the additive build.

More generally, mechanical erosion, chemical erosion, and the combination of mechanical and chemical erosion can remove other (besides alpha case) unwanted contaminants (or debris) from the implant surfaces. FIG. 8 shows how mechanical erosion and the combination of mechanical and chemical erosion can remove unsintered or partially sintered powder from the additive build. FIG. 8 shows SEM images of a surface of a sintered titanium alloy at 250× magnification (top row) and at 1,500× magnification (bottom row). The left column images show the magnified surface off the machine (as additively built) without any follow-up erosion processing. The center column images show the magnified surface following mechanical erosion after the additive build. The right column images show the magnified surface following sequential mechanical erosion and chemical erosion after the additive build.

In addition to imparting micro-scale structural features, mechanical eroding may also remove or reduce debris from the implant surfaces. Acid eroding may also remove or reduce debris from the implant surfaces in addition to imparting nano-scale structural features into implant surfaces. Debris may include external debris such as dirt or other artifacts of handling. External debris may also include particles or components of the media from the mechanical eroding/blasting step, which particles may have become lodged into the implant surface. Debris may also include intrinsic debris, such as artifacts of the additive build process, for example, powder, particles, granules, etc. that were not completely melted or completely sintered during the additive building.

For example, FIG. 8 shows SEM images of a titanium surface created from additive building, with the images in the left column (at two different magnifications) illustrating that some particles have not fully integrated from the additive build. Thus, there is a risk that such particles on an implant may dislodge following implantation, and create negative consequences for the patient either locally or systemically. The erosion process thus may be used to remove unsintered/unmelted or incompletely sintered or melted particles from the surfaces, thereby reducing the risk of particle dislodgement.

As shown in the center column of FIG. 8, mechanical erosion can significantly reduce the amount of un-integrated or partially integrated particles from the surface of the additively built structure. And as shown in the right column of FIG. 8, the addition of chemical erosion (following mechanical erosion) can further reduce the amount of un-integrated or partially integrated particles from the surface of the additively built structure.

After the erosion process step or steps, any protective masking may be removed from the implant, and the eroded and non-eroded surfaces may be cleaned. The surface may also be passivated, for example, using an aqueous solution comprising nitric acid. The surface may be cleaned and rinsed with water.

In preferred aspects, no materials are added onto, impregnated into, embedded into, coated onto, sprayed onto, or otherwise placed on the bone-contacting surfaces. In preferred aspects, no materials are added onto, impregnated into, embedded into, coated onto, sprayed onto, or otherwise placed on the free surfaces. (In fact, the erosion process may be used to remove unwanted contaminants.)

Bone-contacting surfaces and free surfaces that have been produced by additive manufacturing, followed by mechanical erosion, chemical erosion, or both mechanical and chemical erosion comprise an osteoinducting roughness comprising a combination of macro-scale, micro-scale, and nano-scale structures. The additive manufacturing process preferably primarily produces macro-scale features that are specifically engineered into the bone-contacting surfaces being produced during the manufacturing, and the free surfaces produced from the additive manufacturing process are substantially smooth and without these macro-scale structures. Nevertheless, in some aspects, one or more of the free surfaces may comprise macro-scale features, particularly, but not necessarily, when such surfaces are placed in contact with a bone graft material upon implantation. The mechanical and chemical erosion add the micro-scale and nano-scale structures, respectively, to the processed bone-contacting surfaces and to the processed free surfaces. In preferred aspects, mechanical erosion imparts primarily the micro-scale structures into the processed surfaces, and chemical erosion that follows mechanical erosion imparts primarily the nano-scale structures. The bone-contacting surfaces and free surfaces resulting from additive manufacture and mechanical and/or chemical erosion thus include a macro-scale roughness, a micro-scale roughness, and a nano-scale roughness, which may at least partially overlap, or which may substantially overlap, or which may completely overlap. Collectively, these three scales of structural features significantly enhance one or more of stem cell differentiation, preosteoblast maturation, osteoblast development, osteoinduction, and osteogenesis.

Macro-scale structural features include relatively large dimensions, for example, dimensions measured in millimeters (mm), e.g., 1 mm or greater. Micro-scale structural features include dimensions that are measured in microns (μm), e.g., 1 micron or greater, but less than 1 mm. Nano-scale structural features include dimensions that are measured in nanometers (nm), e.g., 1 nanometer or greater, but less than 1 micron. Patterns of macro structural features, micro structural features, and/or nano structural features may be organized in regular and/or repeating patterns and optionally may overlap each other, or such features may be in irregular or random patterns, or repeating irregular patterns (e.g., a grid of irregular patterns).

The additive manufacture and mechanical and chemical erosion steps described herein can be modulated to create a mixture of depths, heights, lengths, widths, diameters, feature sizes, and other geometries suitable for a particular implant application. The orientation of the pattern of features can also be adjusted. Such flexibility is desirable, especially because the ultimate pattern of the osteoinduction-enhancing surfaces may be oriented in opposition to the biologic forces that may be applied against the implant upon implantation, and to the implantation direction.

The macro-scale structural features, micro-scale structural features, and nano-scale structural features are distinct from teeth, spikes, ridges, and other bone-gripping super-macro scale structures that are typically present on the surface of bone-contacting implants. Such teeth, spikes, and ridges are intended to dig into or rake bone. In contrast, the bone-contacting surfaces comprising macro structures as described or exemplified herein, which are produced by additive manufacturing, do not damage or dig into bone as teeth, spikes, ridges, and other bone-gripping super-macro scale structures do. Instead, the bone-contacting surfaces of the invention support a friction-type grip of bone surfaces and inhibit movement of the implant once implanted within the body.

The osteoinducting micro-scale and nano-scale structures on bone-contacting surfaces and on free surfaces produced by mechanical erosion and chemical erosion after additive manufacture enhance and/or facilitate osteoinduction. Additive manufacture followed by mechanical erosion, chemical erosion, or both mechanical and chemical erosion produces or imparts an osteoinducting roughness into bone-contacting and free surfaces that are processed with such erosion. The osteoinducting roughness comprises micro-scale structures and nano-scale structures that combine to promote, enhance, or facilitate the rate and/or the amount of osteoinduction. From this osteoinducting roughness, new bone growth originates from and grows on and out from such processed surfaces of an orthopedic implant. The macro-scale structures on the bone-contacting surfaces of the orthopedic implant grip bone and inhibit movement of the implant within the body and this, in turn, further promotes, enhances, or facilitates the rate and/or the amount of osteoinduction because movement inhibition inhibits the breaking of the incipient bone tissue as the new bone growth proceeds (e.g., unintended movement can disrupt the bone growth process by breaking newly formed bone matrix and tissue).

The enhancement and/or facilitation of osteoinduction from the bone-contacting surfaces and frees surfaces produced by additive manufacture followed by mechanical erosion, chemical erosion, or both mechanical and chemical erosion to impart an osteoinducting roughness is significantly greater than the osteoinduction or the level of enhancement and/or facilitation of osteoinduction that is attained by a surface that has not been subject to either or both of mechanical and chemical erosion. Bone-contacting and/or free surfaces that have not been subject to either or both of mechanical and chemical erosion may be devoid of an osteoinducting roughness comprising micro-scale structures and nano-scale structures. In some aspects, the one or more bone-contacting surfaces produced according to the process (additive manufacture followed by mechanical and/or chemical erosion), when placed in contact with bone, significantly enhance one or more of osteoinduction, osteogenesis, alkaline phosphatase expression by mesenchymal stem cells, osterix expression by preosteoblasts, and osteocalcin expression by osteoblasts, relative to the osteoinduction, osteogenesis, alkaline phosphatase expression by mesenchymal stem cells, osterix expression by preosteoblasts, and/or osteocalcin expression by osteoblasts from an untreated bone-contacting surface (not treated with mechanical and/or chemical erosion), when the untreated surface is placed in contact with bone.

The enhancement and/or facilitation of osteoinduction from the bone-contacting surfaces and frees surfaces produced by additive manufacture followed by mechanical erosion, chemical erosion, or both mechanical and chemical erosion to impart an osteoinducting roughness is significantly greater than the osteoinduction or the level of enhancement and/or facilitation of osteoinduction that is attained by a comparative surface comprising an osteoinducting roughness comprising micro-scale structures and nano-scale structures produced by mechanical erosion, chemical erosion, or both mechanical and chemical erosion of a bulk substrate (i.e., a substrate not produced by additive manufacture). Thus, when an implant is additively manufactured and its surfaces processed/eroded and when a comparative implant is manufactured from a bulk substrate and its surfaces processed/eroded, the osteoinduction from the processed additively manufactured implant may be significantly enhanced over the osteoinduction from the processed bulk substrate.

It is believed that orthopedic implant surfaces that are smooth, or comprise teeth, ridges, grooves, and super-macro structures that are not processed/eroded, or comprise particles, fibers, or powders that have been cold sprayed, thermal sprayed, or affixed with an adhesive thereto, or which otherwise have not been mechanically eroded, chemically eroded, or both mechanically and chemical eroded to impart an osteoinducting roughness comprising micro-scale structures and nano-scale structures, or which otherwise lack an osteoinducting roughness comprising micro-scale structures and nano-scale structures do not significantly enhance osteoinduction, are not osteoinducting, and/or are inferior in their osteoinduction capacity relative to orthopedic implant surfaces produced by additive manufacture followed by mechanical erosion, chemical erosion, or both mechanical and chemical erosion to impart an osteoinducting roughness per the invention. Relatedly, orthopedic implant surfaces that are smooth, or comprise teeth, ridges, grooves, and super-macro structures that are not processed/eroded, or comprise particles, fibers, or powders that have been cold sprayed, thermal sprayed, or affixed with an adhesive thereto, or which otherwise have not been mechanically eroded, chemically eroded, or both mechanically and chemical eroded to impart an osteoinducting roughness comprising micro-scale structures and nano-scale structures, or which otherwise lack an osteoinducting roughness comprising micro-scale structures and nano-scale structures do not significantly enhance osteoinduction, are not osteoinducting, and/or are inferior in their osteoinduction capacity relative to orthopedic implant surfaces produced by mechanical erosion, chemical erosion, or both mechanical and chemical erosion of a bulk substrate.

The osteoinducting micro-scale and nano-scale structures on bone-contacting surfaces and on free surfaces produced by mechanical erosion and chemical erosion after additive manufacture enhance and/or facilitate osteogenesis. Additive manufacture followed by mechanical erosion, chemical erosion, or both mechanical and chemical erosion produces or imparts an osteoinducting roughness into bone-contacting and free surfaces that are processed with such erosion. The osteoinducting roughness comprises micro-scale structures and nano-scale structures that combine to promote, enhance, or facilitate the rate and/or the amount of osteogenesis. From this osteoinducting roughness, new bone growth originates from and grows on and out from such processed surfaces of an orthopedic implant. The macro-scale structures on the bone-contacting surfaces of the orthopedic implant grip bone and inhibit movement of the implant within the body and this, in turn, further promotes, enhances, or facilitates the rate and/or the amount of osteogenesis because movement inhibition inhibits the breaking of the incipient bone tissue as the new bone growth proceeds (e.g., unintended movement can disrupt the bone growth process by breaking newly formed bone matrix and tissue).

The enhancement and/or facilitation of osteogenesis from the bone-contacting surfaces and free surfaces produced by additive manufacture followed by mechanical erosion, chemical erosion, or both mechanical and chemical erosion to impart an osteoinducting roughness is significantly greater than the osteogenesis or the level of enhancement and/or facilitation of osteogenesis that is attained by a comparative surface comprising an osteoinducting roughness comprising micro-scale structures and nano-scale structures produced by mechanical erosion, chemical erosion, or both mechanical and chemical erosion of a bulk substrate. Thus, when an implant is additively manufactured and its surfaces processed/eroded and when a comparative implant is manufactured from a bulk substrate and its surfaces processed/eroded, the osteogenesis from the processed additively manufactured implant may be significantly enhanced over the osteogenesis from the processed bulk substrate.

It is believed that orthopedic implant surfaces that are smooth, or comprise teeth, ridges, grooves, and super-macro structures that are not processed/eroded, or comprise particles, fibers, or powders that have been cold sprayed, thermal sprayed, or affixed with an adhesive thereto, or which otherwise have not been mechanically eroded, chemically eroded, or both mechanically and chemical eroded to impart an osteoinducting roughness comprising micro-scale structures and nano-scale structures, or which otherwise lack an osteoinducting roughness comprising micro-scale structures and nano-scale structures do not significantly enhance osteogenesis, are not osteogeneic, and/or are inferior in their osteogenesis capacity relative to orthopedic implant surfaces produced by additive manufacture followed by mechanical erosion, chemical erosion, or both mechanical and chemical erosion to impart an osteoinducting roughness per the invention. Relatedly, orthopedic implant surfaces that are smooth, or comprise teeth, ridges, grooves, and super-macro structures that are not processed/eroded, or comprise particles, fibers, or powders that have been cold sprayed, thermal sprayed, or affixed with an adhesive thereto, or which otherwise have not been mechanically eroded, chemically eroded, or both mechanical and chemical eroded to impart an osteoinducting roughness comprising micro-scale structures and nano-scale structures, or which otherwise lack an osteoinducting roughness comprising micro-scale structures and nano-scale structures do not significantly enhance osteogenesis, are not osteogeneic, and/or are inferior in their osteogenesis capacity relative to orthopedic implant surfaces produced by mechanical erosion, chemical erosion, or both mechanical and chemical erosion of a bulk substrate.

Osteoinduction may be measured as a function of the level of one or more of alkaline phosphatase (ALP) expression, osterix (OSX) expression, and osteocalcin (OXN) expression. These markers demonstrate the phenotype progression that confirms osteoinduction is occurring. ALP represents an early marker of stem cell differentiation into a preosteoblast. Osterix represents the first bone-specific transcription factor expression (Runx2 is often considered the first transcription factor expressed as a part of the osteoblast differentiation process, although this transcription factor is not specific to bone and influences other biochemical processes within the cell). Osteocalcin represents a mature osteoblast marker. In preferred aspects, the bone-contacting surfaces and free surfaces resulting from additive manufacture, mechanical erosion, and chemical erosion significantly enhance and/or facilitate ALP expression, then osterix expression, and then osteocalcin expression from a stem cell as it differentiates to a preosteoblast and matures to an osteoblast.

Thus, where an implant was additively manufactured and its surfaces processed/eroded and where a comparative implant was manufactured from a bulk substrate and its surfaces processed/eroded, the expression of one or more of ALP, OSX, and OCN from mesenchymal stem cells, preosteoblasts, and osteoblasts, respectively, that have contacted the processed additively manufactured implant surfaces may be significantly enhanced over the expression of one or more of ALP, OSX, and OCN from mesenchymal stem cells, preosteoblasts, and osteoblasts, respectively, that have contacted the processed bulk substrate surfaces.

It is believed that orthopedic implants whose surfaces do not have an osteoinducting roughness comprising micro-scale structures and nano-scale structures produced by mechanical erosion, chemical erosion, or both mechanical and chemical erosion, induce minimal expression of one or more of ALP, OSX, and OCN from mesenchymal stem cells, preosteoblasts, and osteoblasts, respectively, or do not induce expression of one or more of ALP, OSX, and OCN from mesenchymal stem cells, preosteoblasts, and osteoblasts, respectively, at all. Thus, orthopedic implant surfaces that are smooth, or comprise teeth, ridges, grooves, and super-macro structures that are not processed/eroded, or comprise particles, fibers, or powders that have been cold sprayed, thermal sprayed, or affixed with an adhesive thereto, or which otherwise have not been mechanically eroded, chemically eroded, or both mechanically and chemical eroded to impart an osteoinducting roughness comprising micro-scale structures and nano-scale structures, or which otherwise lack an osteoinducting roughness comprising micro-scale structures and nano-scale structures do not significantly enhance the expression of one or more of ALP, OSX, and OCN from mesenchymal stem cells, preosteoblasts, and osteoblasts, respectively, do not induce expression of one or more of ALP, OSX, and OCN from mesenchymal stem cells, preosteoblasts, and osteoblasts, respectively, and/or are inferior in their capacity to induce expression of one or more of ALP, OSX, and OCN from mesenchymal stem cells, preosteoblasts, and osteoblasts, respectively, relative to orthopedic implant surfaces produced by additive manufacture followed by mechanical erosion, chemical erosion, or both mechanical and chemical erosion to impart an osteoinducting roughness per the invention. Relatedly, orthopedic implant surfaces that are smooth, or comprise teeth, ridges, grooves, and super-macro structures that are not processed/eroded, or comprise particles, fibers, or powders that have been cold sprayed, thermal sprayed, or affixed with an adhesive thereto, or which otherwise have not been mechanically eroded, chemically eroded, or both mechanically and chemical eroded to impart an osteoinducting roughness comprising micro-scale structures and nano-scale structures, or which otherwise lack an osteoinducting roughness comprising micro-scale structures and nano-scale structures do not significantly enhance the expression of one or more of ALP, OSX, and OCN from mesenchymal stem cells, preosteoblasts, and osteoblasts, respectively, do not induce the expression of one or more of ALP, OSX, and OCN from mesenchymal stem cells, preosteoblasts, and osteoblasts, respectively, and/or are inferior in their capacity to induce expression of one or more of ALP, OSX, and OCN from mesenchymal stem cells, preosteoblasts, and osteoblasts, respectively, relative to orthopedic implant surfaces produced by mechanical erosion, chemical erosion, or both mechanical and chemical erosion of a bulk substrate.

The following examples are included to more clearly demonstrate the overall nature of the invention. These examples are exemplary, not restrictive, of the invention.

Example 1

SEM Images of Additively Manufactured Titanium Surfaces

Titanium discs were additively manufactured using either laser melting/sintering (e.g., direct metal laser sintering (DMLS)) or electron beam melting (EBM). These discs were then subject to either stress-relief or hot isostatic pressing, and were subject to mechanical and chemical erosion as summarized in Table 1. Scanning electron microscope (SEM) images of the discs were obtained, and are shown in FIGS. 1A, 1B, 1C, 1D, and 1E. (A SEM is an electron microscope in which the surface of a specimen is scanned by a beam of electrons that are reflected to form an image.)

Surface 20A was a DMLS-produced surface that was subject to stress-relief, but no erosion. Surface 20B was an EBM-produced surface that was subject to hot isostatic pressing, but no erosion. Surface 20C was a DMLS-produced surface that was subject to hot isostatic pressing, but no erosion. Surface 22A was a DMLS-produced surface that was subject to stress-relief and mechanical and chemical erosion. Surface 22B was an EBM-produced surface that was subject to hot isostatic pressing and mechanical and chemical erosion. Surface 22C was a DMLS-produced surface that was subject to hot isostatic pressing and mechanical and chemical erosion.

Surface 16E was a laser-produced surface that was subject to hot isostatic pressing and mechanical erosion using a sodium bicarbonate blast. Surface 16F was a laser-produced surface that was subject to hot isostatic pressing and mechanical erosion using a titanium blast. Surface 29D was a laser-produced surface with a built-in macro texture that was subject to hot isostatic pressing and mechanical and chemical erosion.

The SEM images of FIGS. 1A, 1B, 1C, 1D, and 1E show how micro-scale and nano-scale structures are imparted into the titanium surface via the successive mechanical and chemical erosion of the additively manufactured surfaces.

TABLE 1

Additively manufactured surfaces

| #, Manufacture | Post-additive manufacture treatment |
|---|---|
| 20A, DMLS only | Stress-relief |
| 20B, EBM only | HIP |
| 20C, DMLS only | HIP |
| 22A, DMLS followed by mechanical and chemical erosion | Stress-relief |
| 22B, EBM followed by mechanical and chemical erosion | HIP |
| 22C DMLS followed by mechanical and chemical erosion | HIP |
| 16E, laser-produced followed by mechanical erosion | HIP |
| 16F, laser-produced followed by mechanical erosion | HIP |
| 29D, laser-produced followed by mechanical and chemical erosion | HIP |

Example 2

Alkaline Phosphatase, Osterix, and Osteocalcin as Recognized Markers of Osteoblast Development and Osteoinduction Osteogenic differentiation is a continuous process characterized by the rise and fall of several proteins. The proteins analyzed herein characterize early (ALP), mid (OSX) and late (OCN) osteoblast markers. The process of osteoblast differentiation begins with mesenchymal stem cells progressing to an intermediate progenitor capable of undergoing either osteogenesis or chondrogenesis and expressing ALP. These intermediate progenitors that commit to an osteogenic lineage, now termed preosteoblasts, increase the expression of ALP. As the preosteoblast progresses to an osteoblast, the expression of OSX is increased and, finally, once the preosteoblast becomes an osteoblast the expression of OCN is increased.

The osteoblast will eventually mature further and begin transitioning to an osteocyte or undergoing apoptosis. The mature osteoblast state is characterized by a decrease in ALP, and once the osteoblast differentiates to an osteocyte the expression of both OSX and OCN is decreased as well (Baek W-Y et al., J. Bone Miner. Res. 24:1055-65 (2009); Zhang C., J. Orthopaedic Surg. and Res. 5:1 (2010); and Tu Q et al., Tissue Eng'g 1:2431-40 (2007)). In vivo evaluations have revealed that both ALP and OCN are present during fracture healing. In these evaluations, both ALP and OCN production are highest in healing bone fractures at 8 weeks post fracture (Leung K S et al., Bone & Joint Journal 75:288-92 (1993); and Herrmann M. et al., Clin. Chemistry 48:2263-66 (2002)). Furthermore, ALP and OCN have been used for in vitro evaluation of the potential for a synthetic material to promote bone formation in vivo. It has been further demonstrated that increased ALP and OCN in vitro associate with synthetic graft success in vivo (Borden M. et al., J. Biomed. Mater. Res. 61:421-29 (2002); Borden M. et al., Biomaterials. 23:551-59 (2002); and Borden M. et al., J. Bone Joint Surg. Br. 86:1200-08 (2004)). Similar evaluations using titanium mesh have correlated in vitro ALP and osteopontin (a matrix protein secreted earlier in differentiation than OCN) with in vivo success (Datta N., Biomaterials. 26:971-77 (2005); Bancroft G. N., Proc. Natl. Acad. Sci. U.S.A. 99:12600-05 (2002); and Sikavitsas V I et al., J. Biomed. Mater. 67A:944-51 (2003)).

Example 3

Figure 2A:
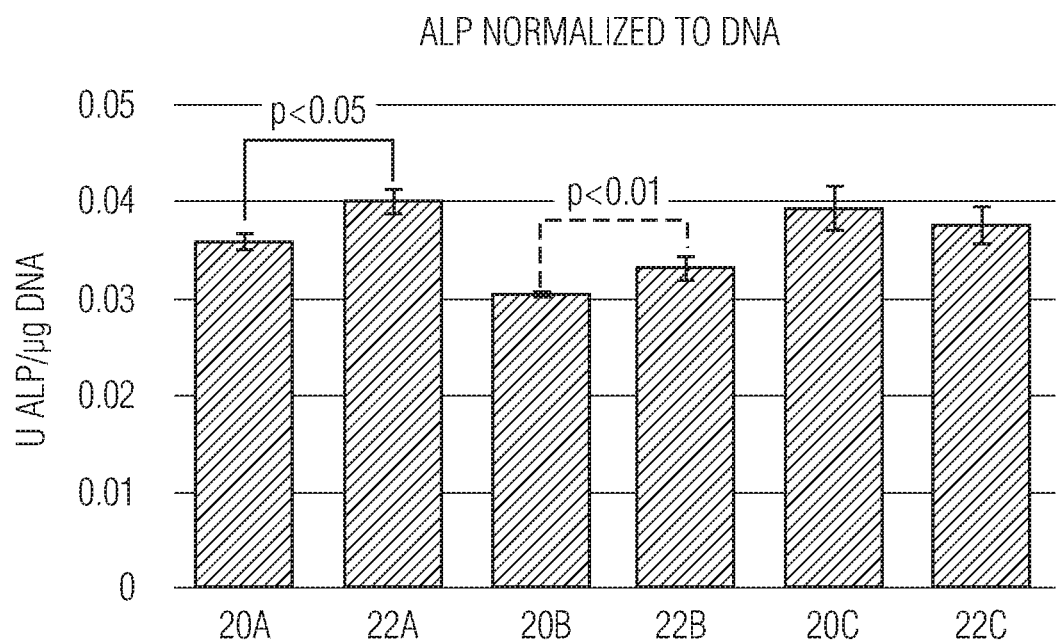
FIG. 2A shows the levels of alkaline phosphatase expressed by MG63 cells cultured on additively manufactured surfaces 20A, 20B, and 20C and 22A, 22B, and 22C (surfaces 20A, 20B, and 20C and 22A, 22B, and 22C are the same surfaces as described in FIGS. 1A, 1B, and 1C)
Figure 2B:
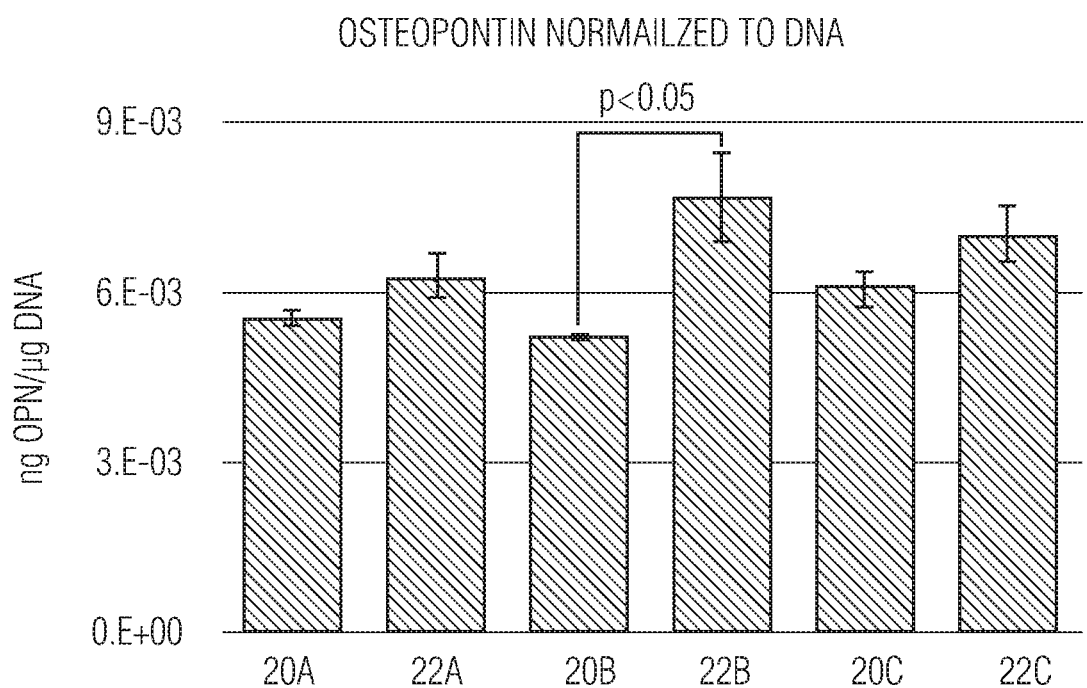
FIG. 2B shows the level of osteopontin expressed by MG63 cells cultured on additively manufactured surfaces 20A, 20B, and 20C and 22A, 22B, and 22C (surfaces 20A, 20B, and 20C and 22A, 22B, and 22C are the same surfaces as described in FIGS. 1A, 1B, and 1C)
Figure 2C:
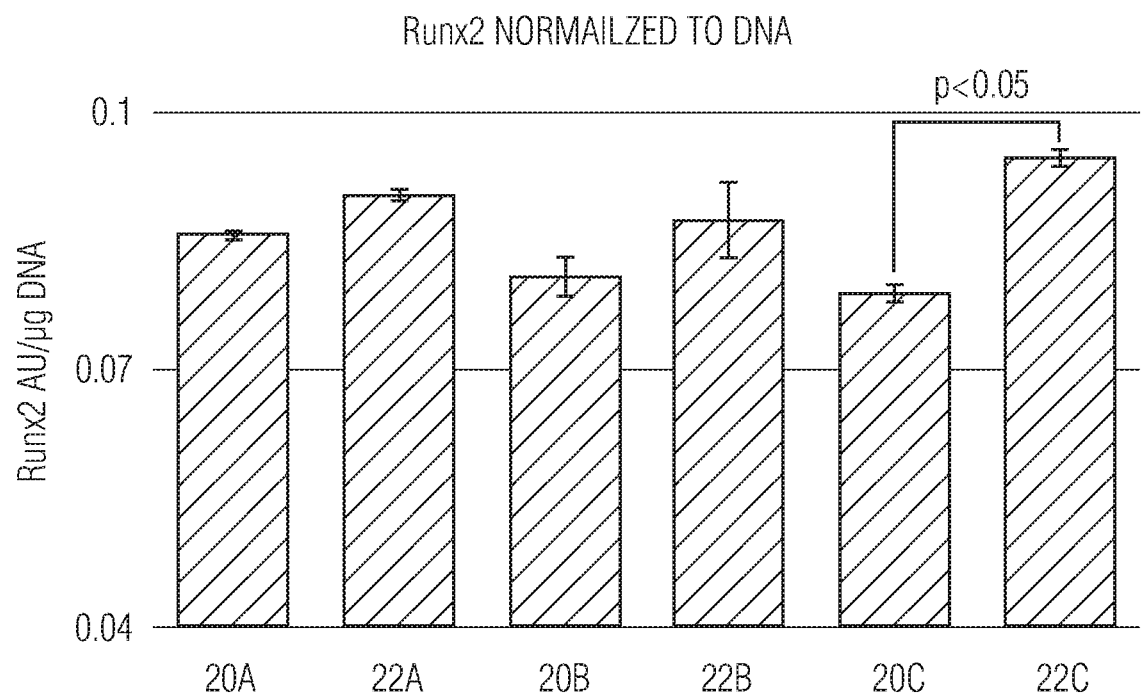
FIG. 2C shows the level of RunX2 expressed by MG63 cells cultured on additively manufactured surfaces 20A, 20B, and 20C and 22A, 22B, and 22C (surfaces 20A, 20B, and 20C and 22A, 22B, and 22C are the same surfaces as described in FIGS. 1A, 1B, and 1C)

Assessment of Osteogenic Markers on MG63 Cells Grown on Osteoinductive Surfaces MG63 cells are a preosteoblast cell line. MG63 cells were seeded onto discs at 10,000 cells/cm$^2$ cultured in EMEM with 10% FBS, 1% Penicillin/Streptomycin, 50 µg/mL Ascorbic Acid, and 10 mM β-Glycerophosphate. After 7 days of culture, the cells were lysed with a Pierce Mammalian Protein Extraction Reagent with protease inhibitors, and lysates were assessed for the expression of alkaline phosphatase (ALP), osteopontin (OPN), and RunX2. Alkaline phosphatase (ALP), an early osteoblast differentiation marker, was measured through an enzymatic assay relying on the conversion of p-Nitrophenyl phosphate to p-Nitrophenol in the presence of ALP and then measuring the absorbance of p-Nitrophenol. ALP was normalized to the amount of DNA present in the samples. DNA was measured with a standard PicoGreen assay. Osteopontin (OPN), a protein expressed by osteoblasts throughout differentiation, was measured through quantitative Western blotting and normalized to tubulin. The results are shown in FIGS. 2A, 2B, and 2C. The surface key for FIGS. 2A-2C is shown in Table 1.

FIG. 2A shows the levels of alkaline phosphatase expressed by MG63 cells cultured on additively manufactured surfaces 20A, 20B, and 20C and 22A, 22B, and 22C. FIG. 2B shows the level of osteopontin expressed by MG63 cells cultured on additively manufactured surfaces 20A, 20B, and 20C and 22A, 22B, and 22C. FIG. 2C shows the level of RunX2 expressed by MG63 cells cultured on additively manufactured surfaces 20A, 20B, and 20C and 22A, 22B, and 22C. Surfaces 20A, 20B, and 20C and 22A, 22B, and 22C are the same surfaces as described in FIGS. 1A, 1B, and 1C.

As shown, the additively manufactured (DMLS and EBM) and processed (mechanically and chemically eroded) surfaces were significantly better than additively manufactured but not processed surfaces in terms of ALP, RunX2, and OPN expression.

Example 4

Assessment of Osteogenic Markers on SaOS-2 Cells Grown on Osteoinductive Surfaces SAOS-2 cells were obtained from ATCC (Manassas, Va.); PicoGreen Assays, McCoy's 5A media and Penicillin/Streptomycin were all obtained from Life Technologies (Carlsbad, Calif.); fetal bovine serum was obtained from Atlanta Biologicals (Atlanta, Ga.); alkaline phosphatase assay was obtained from Bio-Rad (Hercules, Calif.); Osterix ELISA was obtained from LifeSpan BioSciences (Seattle, Wash.); and Osteocalcin ELSIA was obtained from R&D Systems (Minneapolis, Minn.).

SAOS-2 cells were maintained in basal growth media consisting of McCoy's 5A supplemented with 15% FBS and 1% Penicillin/Streptomycin. Once appropriate numbers of cells were reached in culture, the SAOS-2 cells were seeded on titanium disc surfaces (Table 1) at a density of 10,000 cells/cm$^2$. SAOS-2 cells were cultured on each surface type for seven days, and media were changed every two days. At day 7, the media were frozen for further analysis and the SAOS-2 cells were lysed in RIPA buffer (150 mM sodium chloride, 1% v/v TRITON® X-100 non-ionic surfactant, 0.5% w/v sodium deoxycholate, 0.1% w/v sodium dodecyl sulfate, 50 mM Trizma base, pH 8.0).

Cellular DNA was quantified using a PicoGreen Assay following the manufacturer's protocol. Alkaline phosphatase (ALP) was assayed through the ALP catalyzed conversion of p-nitrophenylphosphate to p-nitrophenol following the manufacturer's protocol. Both osterix (OSX) and osteocalcin (OCN) were quantified using and ELISA assay and following the manufacturer's protocol. Runx2 and OPN were also assayed, but neither demonstrated any substantial trend or significant data (data not shown); these are both very early osteoblast markers. The results are shown in FIGS. 3A, 3B, 3C, and 3D. The surface key for FIGS. 3A-3D is shown in Table 1.

Figure 3A:
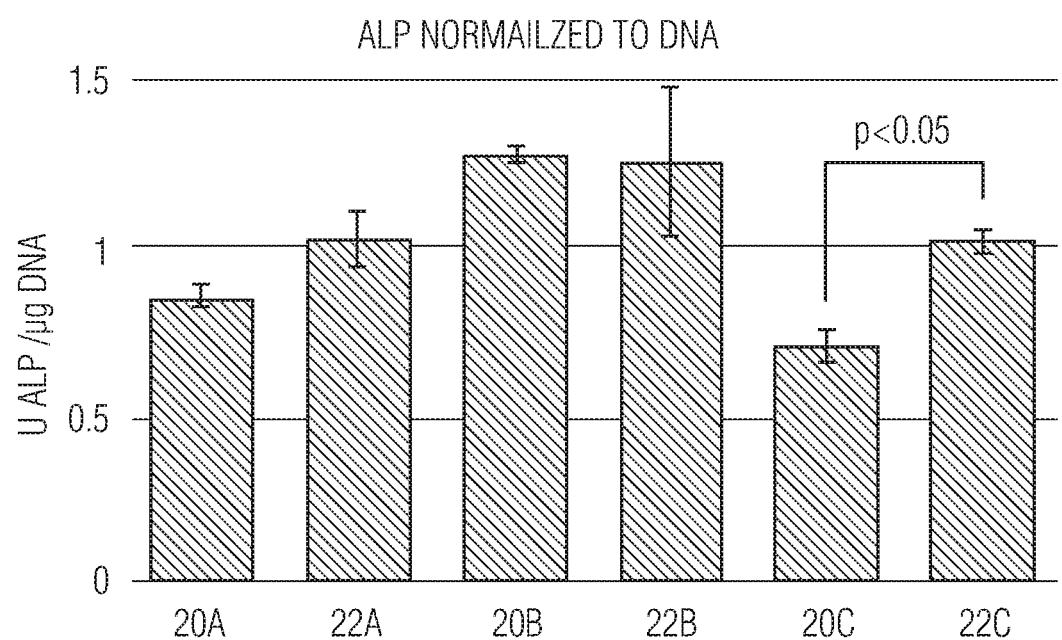
FIG. 3A shows the levels of alkaline phosphatase expressed by SAOS-2 cells cultured on additively manufactured surfaces 20A, 20B, and 20C and 22A, 22B, and 22C (surfaces 20A, 20B, and 20C and 22A, 22B, and 22C are the same surfaces as described in FIGS. 1A, 1B, and 1C)
Figure 3B:
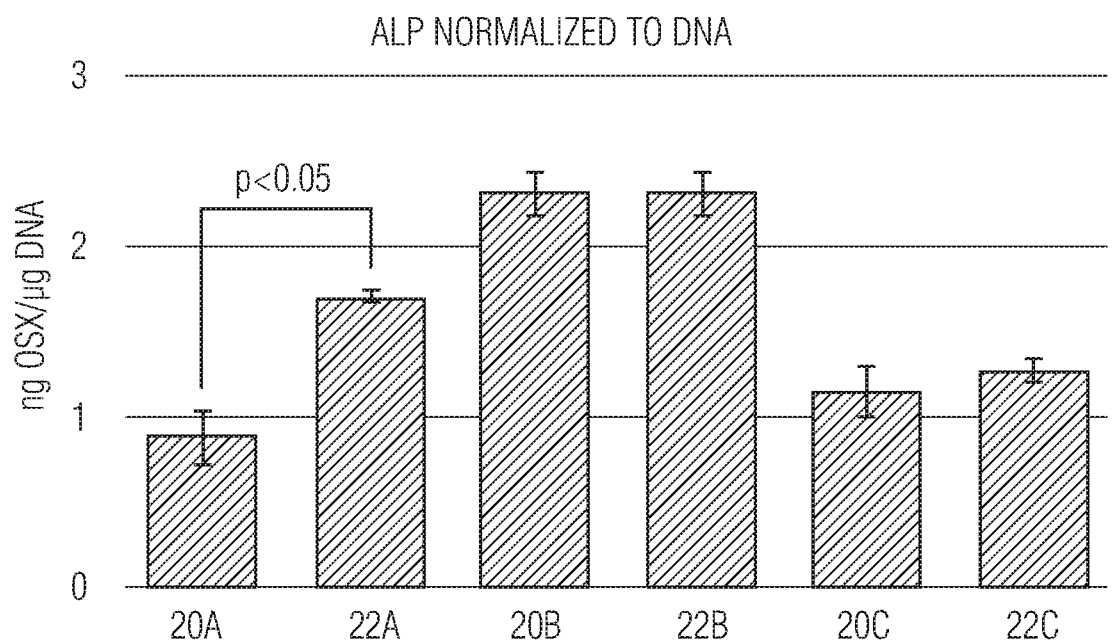
FIG. 3B shows the levels of osterix expressed by SAOS-2 cells cultured on additively manufactured surfaces 20A, 20B, and 20C and 22A, 22B, and 22C (surfaces 20A, 20B, and 20C and 22A, 22B, and 22C are the same surfaces as described in FIGS. 1A, 1B, and 1C)
Figure 3C:
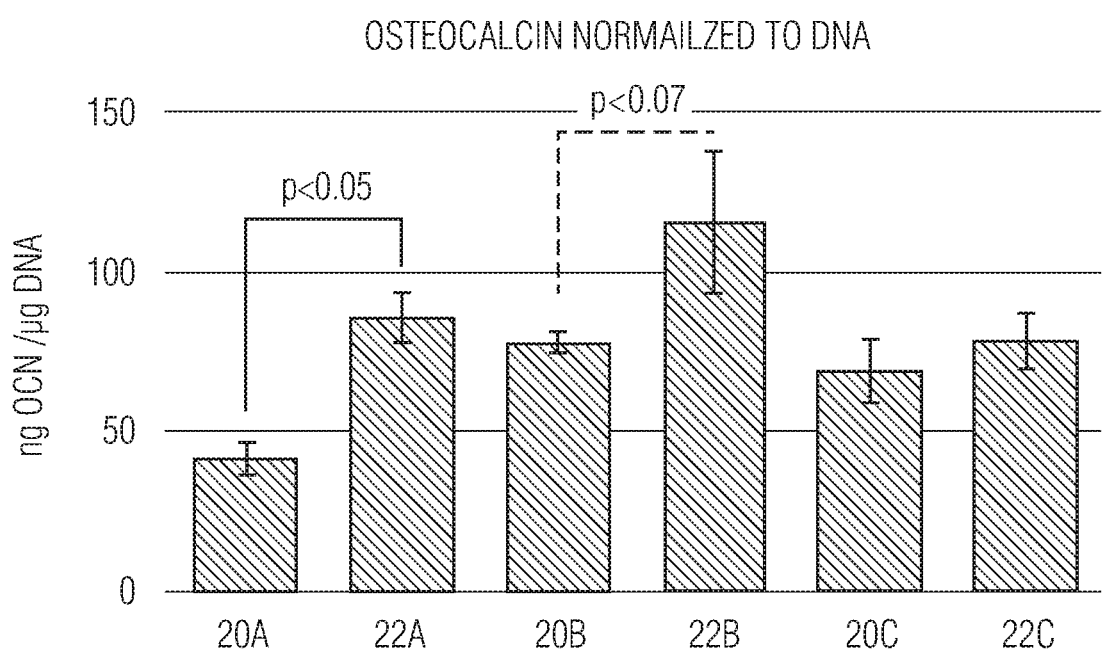
FIG. 3C shows the levels of osteocalcin expressed by SAOS-2 cells cultured on additively manufactured surfaces 20A, 20B, and 20C and 22A, 22B, and 22C (surfaces 20A, 20B, and 20C and 22A, 22B, and 22C are the same surfaces as described in FIGS. 1A, 1B, and 1C)
Figure 3D:
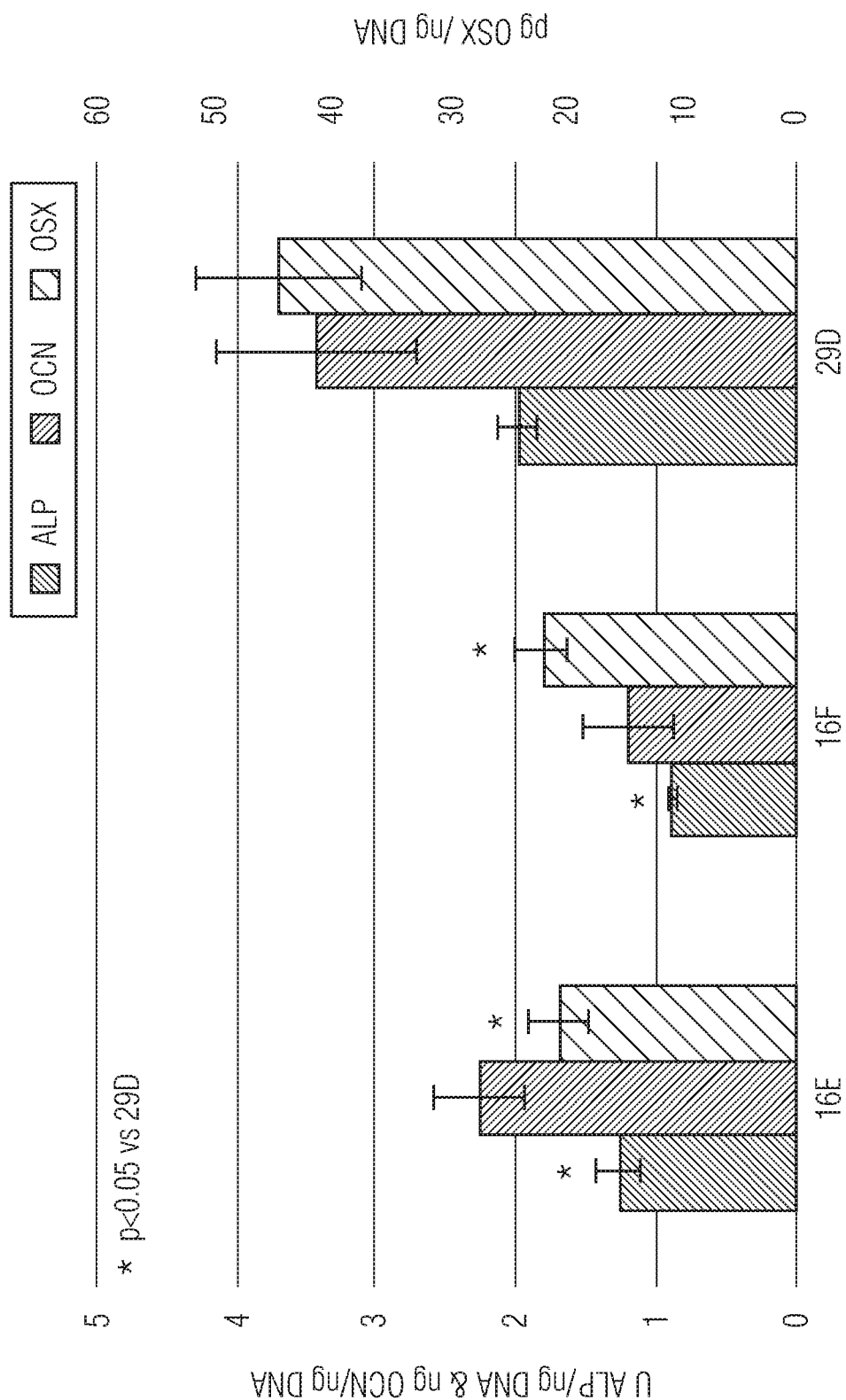
FIG. 3D shows the levels of alkaline phosphatase (leftmost bar), osterix (center bar), and osteocalcin (right-most bar) expressed by SAOS-2 cells cultured on additively manufactured surfaces 16E, 16F, and 29D, respectively (surfaces 16E, 16F, and 29D are the same surfaces as described in FIGS. 1D and 1E)

FIG. 3A shows the levels of alkaline phosphatase expressed by SAOS-2 cells cultured on additively manufactured surfaces 20A, 20B, and 20C and 22A, 22B, and 22C. FIG. 3B shows the levels of osterix expressed by SAOS-2 cells cultured on additively manufactured surfaces 20A, 20B, and 20C and 22A, 22B, and 22C. FIG. 3C shows the level of osteocalcin expressed by SAOS-2 cells cultured on additively manufactured surfaces 20A, 20B, and 20C and 22A, 22B, and 22C. FIG. 3D shows the levels of alkaline phosphatase (left-most bar), osterix (center bar), and osteocalcin (right-most bar) expressed by SAOS-2 cells cultured on additively manufactured surfaces 16E, 16F, and 29D, respectively. Surfaces 20A, 20B, 20C, 22A, 22B, 22C, 16E, 16F, and 29D are the same surfaces as described in FIGS. 1A, 1B, 1C, 1D, and 1E.

As shown in FIGS. 3A, 3B, and 3C, all additively manufactured and processed (mechanically and chemically eroded) surfaces demonstrated improved expression of the ALP, OSX, and OCN markers relative to surfaces that were additively manufactured without processing (mechanically and chemically erosion). Processing of additively manufactured surfaces significantly enhanced osteoblast differentiation, as demonstrated by the ALP, OSX, and OCN markers, relative to additively manufactured surfaces without erosion. As shown in FIG. 3D, the additively manufactured and processed (mechanically and chemically eroded) surface 29D demonstrated improved expression of the ALP, OSX, and OCN markers relative to surfaces 16E and 16F that were additively manufactured and processed with only mechanical but not chemical erosion.

Although illustrated and described above with reference to certain specific embodiments and examples, the present invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges. It is also expressly intended that the steps of the processes of manufacturing the various devices disclosed above are not restricted to any particular order unless specifically and otherwise stated.

What is claimed:

1. An orthopedic implant having a titanium or titanium alloy body with a plurality of surfaces, the orthopedic implant produced according to a process comprising the operations of:
    (a) additively building the orthopedic implant; and then
    (b) treating the orthopedic implant with hot isostatic pressure or hot uniaxial pressure; and then
    (c) mechanically, chemically, or mechanically and chemically eroding one or more surfaces of the orthopedic implant to (i) remove alpha case from, and (ii) impart an osteoinducting roughness including micro-scale structures and nano-scale structures into, the one or more surfaces.

2. The orthopedic implant according to claim 1, wherein the one or more surfaces include surfaces within the interior of the body of the orthopedic implant.

3. The orthopedic implant according to claim 1, wherein the one or more surfaces are configured to contact a bone or a bone graft material.

4. The orthopedic implant according to claim 1, wherein the one or more surfaces are free surfaces.

5. The orthopedic implant according to claim 1, wherein the operation (c) further comprises mechanically eroding the one or more surfaces of the orthopedic implant and, thereafter, chemically eroding the one or more surfaces.

6. The orthopedic implant according to claim 5, wherein mechanically eroding the one or more surfaces of the orthopedic implant imparts the micro-scale structures into the one or more surfaces and chemically eroding the one or more surfaces of the orthopedic implant imparts the nano-scale structures into the one or more surfaces.

7. The orthopedic implant according to claim 6, wherein the chemically eroded nano-scale structures overlap with the mechanically eroded micro-scale structures.

8. The orthopedic implant according to claim 7, wherein the operation (a) of additively building the orthopedic implant yields macro-scale structures, which inhibit movement of the orthopedic implant, and the micro-scale structures, and the nano-scale stuctures overlap each other.

9. The orthopedic implant according to claim 1, wherein treating comprises heating the implant to a temperature less than 80% of a melting temperature of the titanium or titanium alloy from which the implant is made, and at a pressure of at least 100 MPa.

10. The orthopedic implant according to claim 1, wherein the treating step is completed under vacuum or in an inert gas.

11. The orthopedic implant according to claim 1, wherein the process further comprises the operation of applying a coating to the additively built orthopedic implant, before further processing, to block carbon, nitrogen, and oxygen from the one or more surfaces to be further processed.

12. The orthopedic implant according to claim 1, wherein the operation (a) of additively building the orthopedic implant is completed by melting powder, particles, granules, wires, fragments, or combinations thereof of the titanium or titanium alloy into the shape of the orthopedic implant.

13. The orthopedic implant according to claim 1, wherein the operation (a) of additively building the orthopedic implant is completed by sintering powder, particles, granules, wires, fragments, or combinations thereof of the titanium or titanium alloy into the shape of the orthopedic implant.

14. The orthopedic implant according to claim 1, wherein the operation (a) of additively building the orthopedic implant comprises vertically additively building the orthopedic implant.

15. An orthopedic implant having a titanium or titanium alloy body with a plurality of surfaces, the orthopedic implant produced according to a process comprising the operations of:
 (a) additively building the orthopedic implant having one or more free surfaces and having one or more bone-contacting surfaces adapted to be placed in contact with bone, at least the one or more bone-contacting surfaces having a macro-scale roughness that inhibits movement of the orthopedic implant when the bone-contacting surfaces are placed in contact with bone; and then
 (b) treating the orthopedic implant with hot isostatic pressure or hot uniaxial pressure to collapse any inclusions present in the orthopedic implant;
 (c) sequentially mechanically and chemically eroding one or more of the one or more free surfaces and the one or more bone-contacting surfaces to (i) remove alpha case from, and (ii) impart an osteoinducting roughness including micro-scale structures and nano-scale structures into, one or more of the one or more free surfaces and the one or more bone-contacting surfaces.

16. The orthopedic implant according to claim 15, wherein the macro-scale structures, the micro-scale structures, and the nano-scale structures overlap each other.

17. The orthopedic implant according to claim 15, wherein treating comprises heating the implant to a temperature ranging from 1,643° F. to 1,751° F.±59° F. at a pressure of at least 100 MPa for a period of 180±60 minutes and then cooling to below 797° F.

18. The orthopedic implant according to claim 15, wherein the treating step is completed under vacuum or in an inert gas.

19. The orthopedic implant according to claim 15, wherein the process further comprises the operation of applying a coating to the additively built orthopedic implant, after the operation (a) and before further processing, to block carbon, nitrogen, and oxygen from the one or more surfaces to be further processed.

20. The orthopedic implant according to claim 15, wherein the operation (a) of additively building the orthopedic implant is completed by melting or sintering powder, particles, granules, wires, fragments, or combinations thereof of the titanium or titanium alloy into the shape of the orthopedic implant.

* * * * *